(12) United States Patent
Schelkanova et al.

(10) Patent No.: US 11,675,177 B2
(45) Date of Patent: Jun. 13, 2023

(54) SPATIAL PHASE FILTER AND ILLUMINATION DEVICE FOR DEEP INTERROGATION OF STRONGLY SCATTERING MEDIA AND USES THEREOF

(71) Applicant: Ryerson University, Toronto (CA)

(72) Inventors: Irina Schelkanova, Toronto (CA); Aditya Pandya, Toronto (CA); Zeev Zalevsky, Rosh ha Ayin (IL); Alexandre Douplik, Toronto (CA)

(73) Assignee: RYERSON UNIVERSITY, Toronto (CA)

( * ) Notice: Subject to any disclaimer, the term of this patent is extended or adjusted under 35 U.S.C. 154(b) by 10 days.

(21) Appl. No.: 17/259,494

(22) PCT Filed: Jul. 10, 2019

(86) PCT No.: PCT/CA2019/050951
§ 371 (c)(1),
(2) Date: Jan. 11, 2021

(87) PCT Pub. No.: WO2020/010457
PCT Pub. Date: Jan. 16, 2020

(65) Prior Publication Data
US 2021/0302713 A1    Sep. 30, 2021

Related U.S. Application Data

(60) Provisional application No. 62/696,519, filed on Jul. 11, 2018.

(51) Int. Cl.
| | |
|---|---|
| *G02B 21/36* | (2006.01) |
| *G02B 6/08* | (2006.01) |
| *G02B 21/00* | (2006.01) |
| *G02B 21/08* | (2006.01) |
| *H01L 27/146* | (2006.01) |

(52) U.S. Cl.
CPC ............. *G02B 21/362* (2013.01); *G02B 6/08* (2013.01); *G02B 21/0008* (2013.01); *G02B 21/084* (2013.01); *H01L 27/14625* (2013.01)

(58) Field of Classification Search
CPC combination set(s) only.
See application file for complete search history.

(56) References Cited

U.S. PATENT DOCUMENTS

| | | | |
|---|---|---|---|
| 5,594,828 A | 1/1997 | Nielsen et al. | |
| 6,895,077 B2* | 5/2005 | Karellas | H04N 5/32 |
| | | | 378/98.12 |

(Continued)

FOREIGN PATENT DOCUMENTS

EP          297798 B1 *  9/1994  ........... H04N 1/0311

OTHER PUBLICATIONS

Notification of Transmittal of International Search Report—PCT/CA2019/050951 Jul. 10, 2019—Ryerson University.

(Continued)

*Primary Examiner* — William C Vaughn, Jr.
*Assistant Examiner* — Naod W Belai
(74) *Attorney, Agent, or Firm* — Kramer & Amado, P.C.

(57) ABSTRACT

An imaging sensing system containing:
i) a fibre optic plate (FOP) having a proximal end, a distal end and a body situated between the proximal and distal ends;
ii) at least one illumination component, and
ii) an image sensor proximate the FOP.

19 Claims, 19 Drawing Sheets

(56) References Cited

U.S. PATENT DOCUMENTS

| | | | |
|---|---|---|---|
| 9,285,545 B2 | 3/2016 | Rigney | |
| 9,933,565 B2* | 4/2018 | Swihart | G02B 6/08 |
| 2005/0131400 A1* | 6/2005 | Hennings | A61B 18/24 |
| | | | 606/15 |
| 2015/0207974 A1* | 7/2015 | Mody | H04N 5/35581 |
| | | | 348/296 |
| 2016/0247010 A1* | 8/2016 | Huang | G06V 40/1365 |
| 2019/0195790 A1* | 6/2019 | Petitdidier | A61B 5/0075 |

OTHER PUBLICATIONS

IOP Science: Diffuse reflectance measurements using lensless CMOS Imaging chip; Journal of Physics: Conference Series 541 (2014) Schelkanova et al.

Optical Detection of a Capillary Grid Spatial Pattern in Epithelium by Spatially Resolved Diffuse Reflectance Probe: Monte Carlo Verification—Journal of Selected Topics in Quantum Electronics,ol 20, No. 2, Mar./Apr. 2014—Guennadi Saiko et al.

Real time Optical Monitoring of Capilarry Grid Spatial Pattern in Epithelium By Spatially Resolved Diffuse Reflectance Probe—Journal of Innovative Optical Health Sciences—Jun. 2012.

Reflectance of Biological Turbid Tissues under Wide Area Illumination: Single Backward Scattering Approach—Guennadi Saiko et al. Department of Physics, Ryerson University; Published Mar. 10, 2014.

Spatially Resolved, Diffuse Reflectance Imaging for Subsurface Pattern Visualization Toward Development of a Lensless imaging Platform: Phantom Experiments—Journal of Biomedical Optics 21(1), 015004 (Jan. 2016); Irina Schelkanova et al.

* cited by examiner

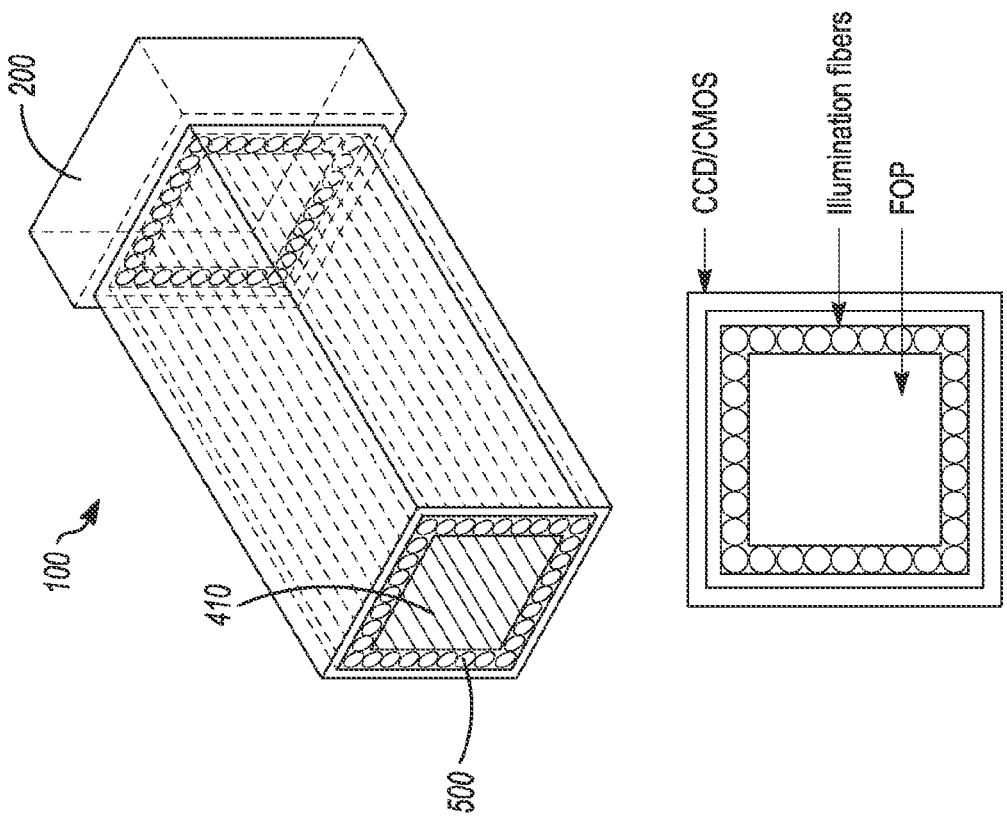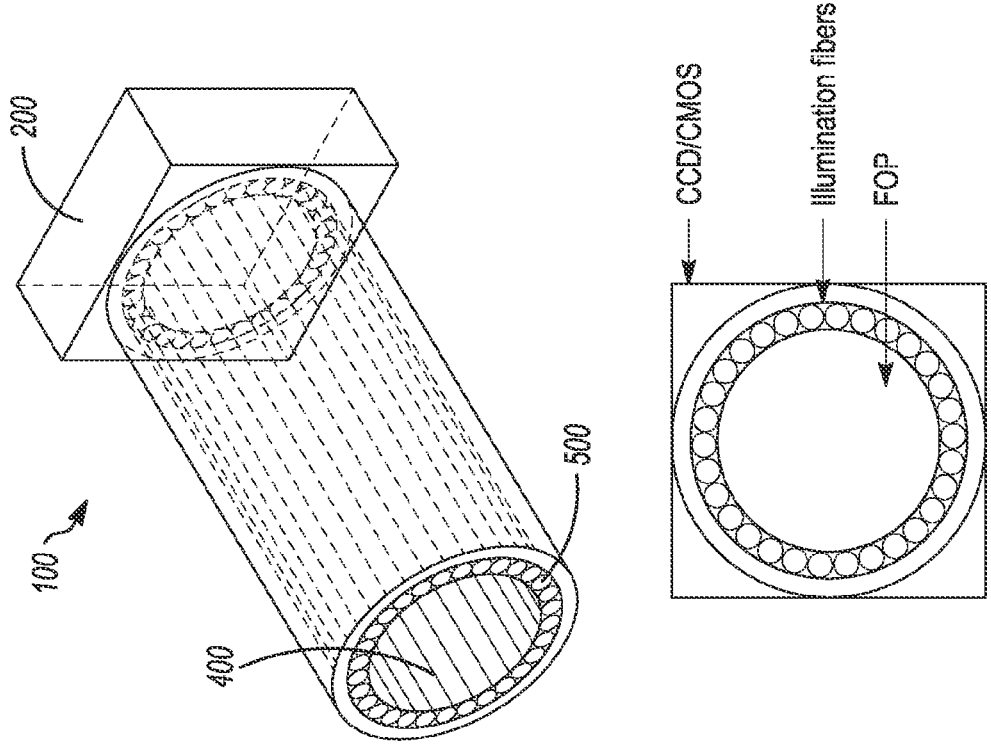
FIG. 2

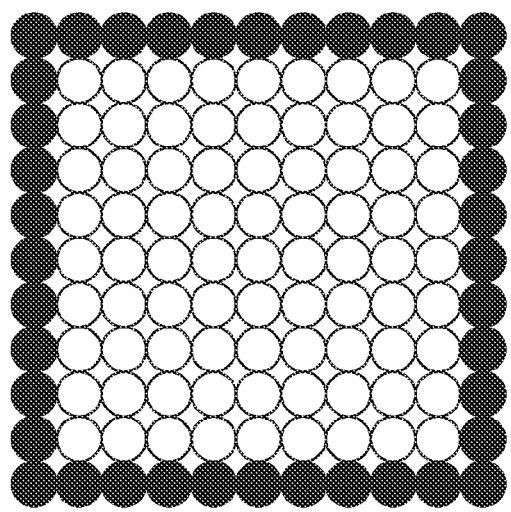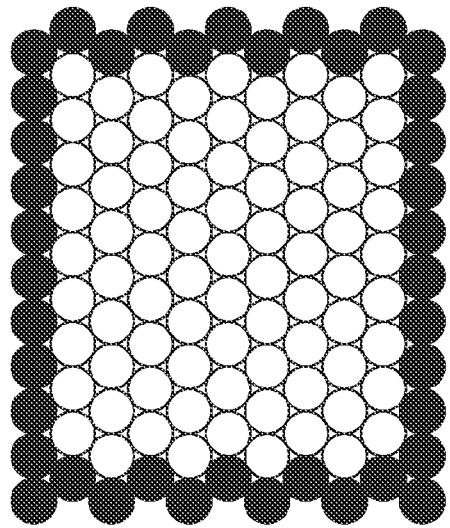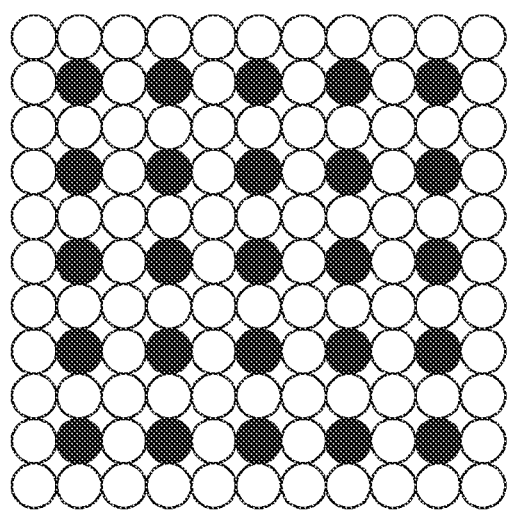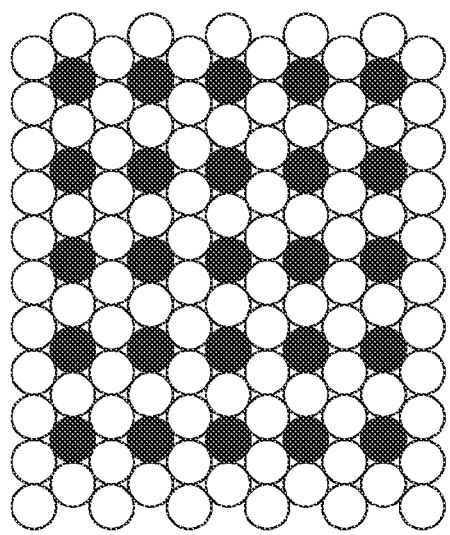
Square / rectangular packing
Hexagonal tight packing
FIG. 3B

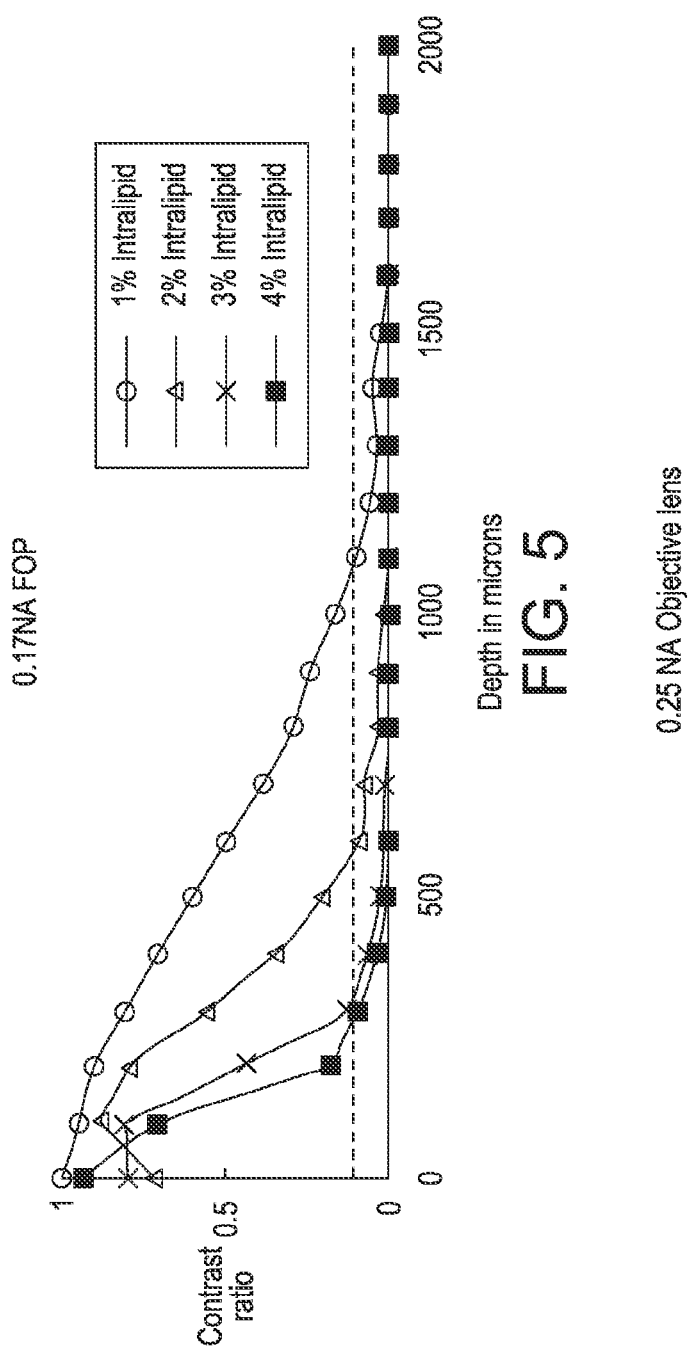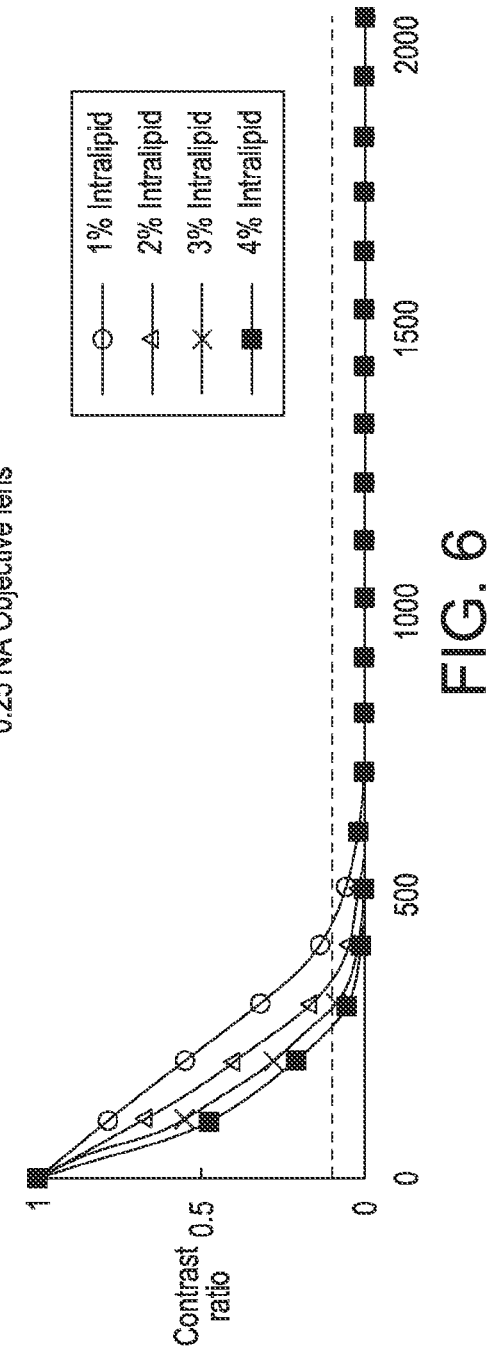

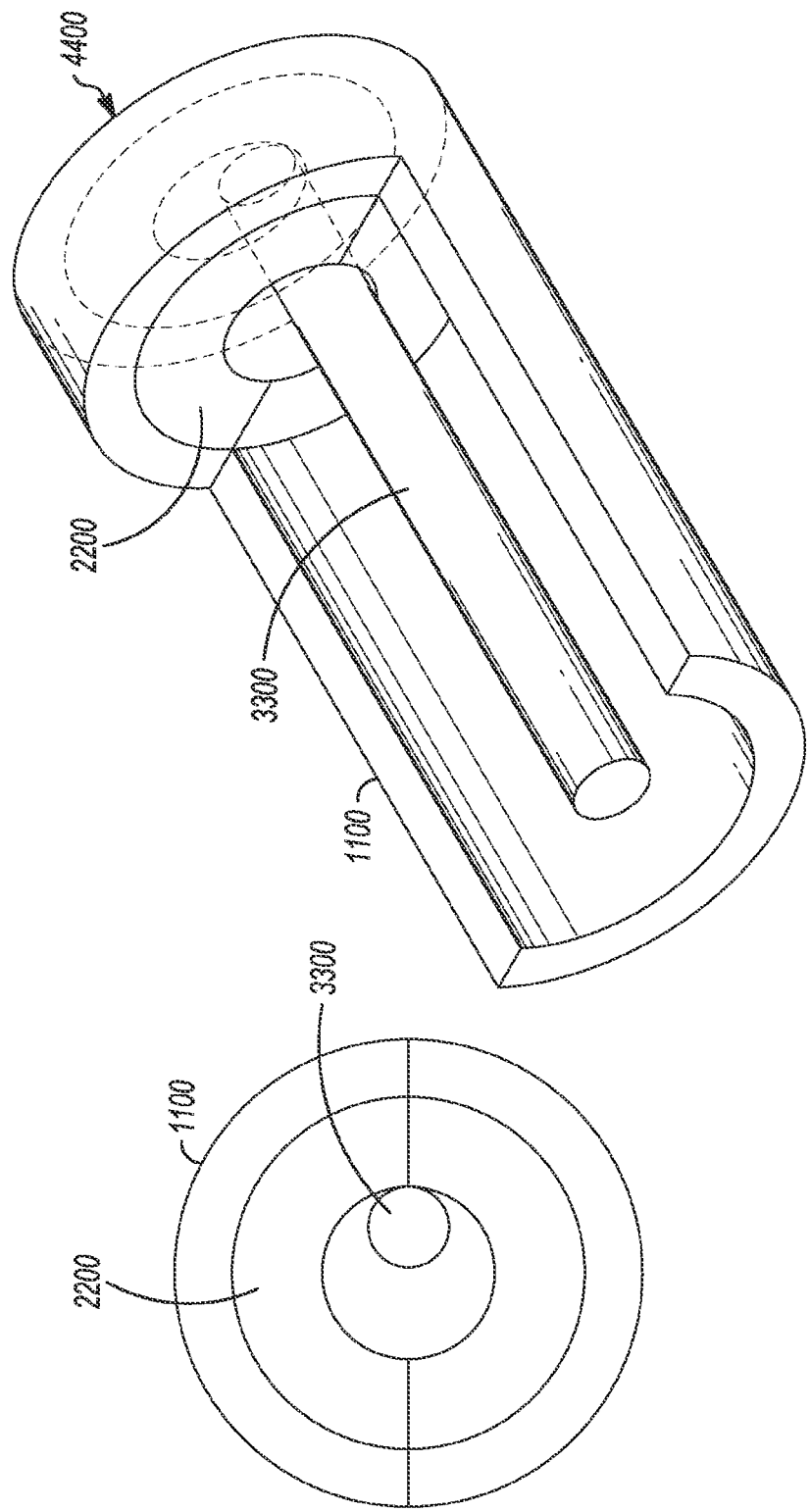

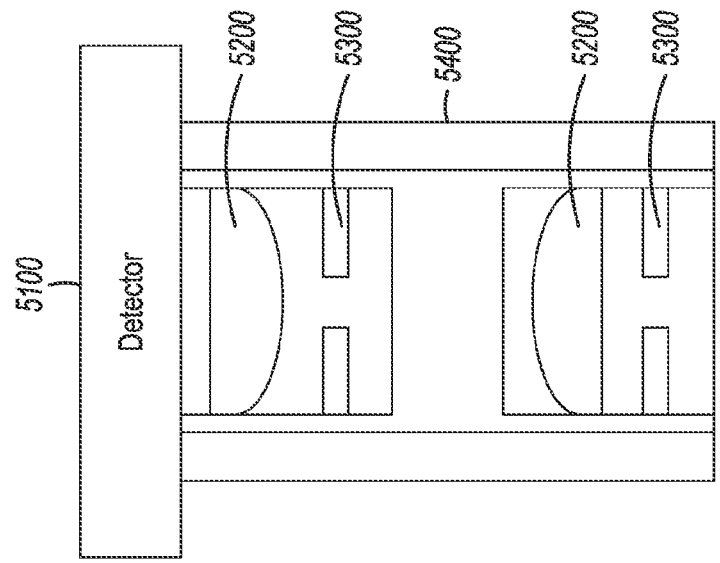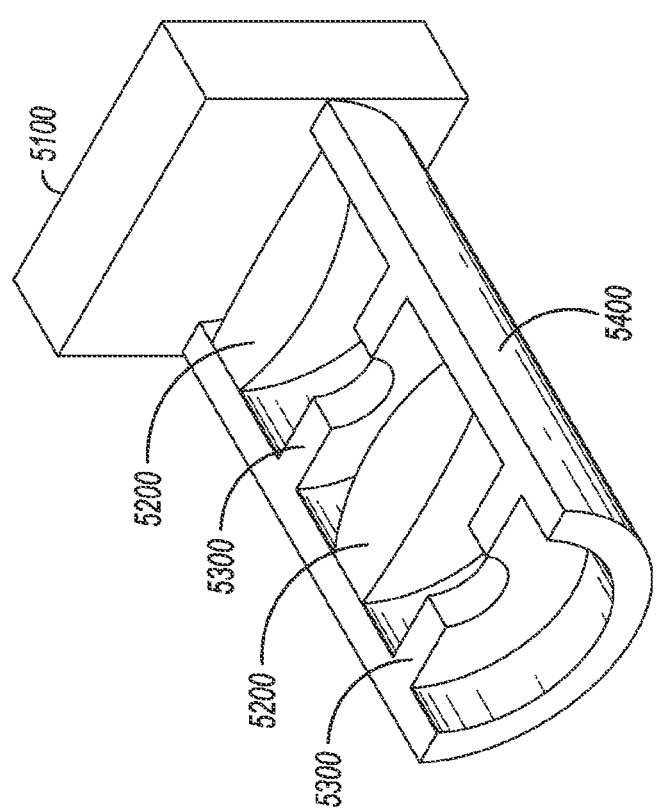
FIG. 12A

SPATIAL PHASE FILTER AND ILLUMINATION DEVICE FOR DEEP INTERROGATION OF STRONGLY SCATTERING MEDIA AND USES THEREOF

FIELD OF THE DISCLOSURE

The disclosure relates to optical physics and optical engineering and the filtering of scattered photons to achieve deeper interrogation of an area within scattering media.

BACKGROUND

Imaging with sufficient resolution of an object embedded in a turbid medium requires controlling the effect of scattered light within the turbid medium so that only ballistic (no or insignificantly scattered) light that has traveled via region of interest is detected. The existing methods for gating such "ballistic" and "quasi-ballistic" photons in diffuse reflectance imaging set-ups include time gating [E. M. Hillman, J. C. Hebden, M. Schweiger, H. Dehghani, F. E. Schmidt, D. T. Delpy, and S. R. Arridge, "Time resolved optical tomography of the human forearm," Phys Med Biol, vol. 46, no. 4. pp. 1117-1130, 2001], [A. M. Zysk, F. T. Nguyen, A. L. Oldenburg, D. L. Marks. and S. A. Boppart, "Optical coherence tomography: a review of clinical development from bench to bedside," Journal of Biomedical Optics, vol. 12. p. 51403, 2007], coherence gating [G. Indebetouw and P. Klysubun, imaging through scattering media with depth resolution by use of low-coherence gating in spatiotemporal digital holography," Opt. Lett., vol. 25, no. 4, pp. 212-214, 2000], polarization gating (O'Doherty. J. Henricson, J., Anderson, C., Leahy, M. J., Nilsson. G. E. and Sjøberg, F. (2007). Sub-epidermal imaging using polarized light spectroscopy for assessment of skin microcirculation. Skin Research and Technology, 13: 472-484. doi:10.1111/j.1600-0846.2007.00253.x). angle gating using barriers (S. P Schilders, X. S. Gan, and M. Gu, "Microscopic imaging through a turbid medium by use of annular objectives for angle gating," Appl. Opt., vol. 37, no. 22, pp. 5320-5326, 1998,) and physical barrier gating created by fine hole array [G H Chapman. B. Kaminska. P. K. Y. Chan, F. Vasefi, and N. Pfeiffer, "Angular filters for optical tomography of highly scattering media." US20080177169A1. July-2008]. When these methods are implemented in diffuse reflectance imaging applications, and in microscopic imaging systems. gating the relevant photons can become very complex and costly.

One of the established methods in the field of biomedical imaging is Diffuse Optical Tomography (DOT) [J. Culver, G. Perry, and B. Zeff, "High performance imaging system for diffuse optical tomography and associated method of use." U.S. Pat. No. 7,983,740B2, July-2011], [T. Koehler, T. Nielsen, B. J. Brendel, A. Ziegler, R. Ziegler, L. P. Bakker, and D. M. M. B. Van, "Device for imaging the interior of an optically turbid medium and receptacle unit for such a device." U.S. Pat. No. 9,488,574B2, April-2009]. The technique utilizes near infra-red light to image large tissue volumes such as the breast or brain [R. Kiesslich, M. Goetz, A. Hoffman, and P. R. Galle, "New imaging techniques and opportunities in endoscopy." Nature Reviews Gastroenterology and Hepatology. 2011], [C. Balas. "Review of biomedical optical imaging—a powerful, non-invasive, non-ionizing technology for improving in vivo diagnosis." Meas. Sci. Technol., vol. 20, p. 104020, 2009]. DOT relies on a model of light scattering to compensate the statistically uncertain paths of photons as they travel through the tissue. This uncertainty manifests as blurring in the reconstructed images, such that resolutions between 0.5-10 mm are typical. As the near infra-red range of light is significantly less absorbing and scattering as compared to the visible range, this may also limit the ability of DOT to detect many of the object's intrinsic light absorption contrast based features, which main absorption is in the visible range.

The above mentioned category of work performed for imaging through scattering media is termed Angular Domain Imaging (ADI) [Chapman et al., "Angular filters for optical tomography of highly scattering media." US20080177169A1, July-2008]. [F. Vasefi, B. Kaminska, G. H. Chapman, and J. J. L. Carson, "Image contrast enhancement in angular domain optical imaging of turbid media," Opt. Express, vol. 16, no. 26, pp. 21492-21504, 2008]. ADI is an optical tomography, trans-illumination method, which introduces spatial filtering of the detected photons to reject the photons, which do not fall within a specified angle by Angular Filter Array (AFA) device for trans-illumination, which actually is a fine hole (tunnel or channel) array that provides separation of scattered versus non-scattered photons to improve resolution and contrast of diffuse images. These micro-tunnels (micro-collimators) physically filter the light reducing the numerical aperture (NA) of the light collection cone. Only the light that travels within the tunnel is allowed to reach the detector. Rejection of the light is achieved via micro machined Angular Filter Array tunnels. The aspect ratio of each micro channel (length/width) determines the acceptance angle, which is typically =0.3 degree (NA=0.005) [Chapman et al., "Angular filters for optical tomography of highly scattering media." Google Patents. July-2008]. An image is formed from non-scattered photons. This method is capable of resolving 153 µm structures [Chapman et al., "Angular filters for optical tomography of highly scattering media," US20080177169A1, July-2008]. Resolution of the system depends on the physical parameters of the tunnels and scanning step size. A serious limitation of this system is that in order to compose a two-dimensional (2D) image, a linear array of tunnels must be scanned over an object, which creates uncertainty of misalignment of each following scan with the previous scan, which makes applicability of this method in non-stationary media practically impossible. Another disadvantage is the limit on the width of the tunnels after which the light will not pass unobstructed. The diffraction of the light occurring on the edges of very narrow tunnels cause significant blurring of the image. Alignment of the collimated source and the detector is a strict requirement to produce good signal-to-noise images. Laser illumination has to be restricted to the AFA area to prevent higher scattering background interference with the image. Another significant limitation of this method is its ability to scale the tunnel size as manufacturing tunnels close to a micron is very challenging.

A third category is lens-based systems, where applying large numerical apertures (NA), light collection provides a high imaging resolution but small focal and interrogation depths. There have been various approaches towards angle gating using a lens-based assembly. Generally, these methods focus on using objectives with apertures (annular/spherical apertures) to perform angular gating [S. P. Schilders, X. S. Gan, and M. Gu, "Microscopic imaging through a turbid medium by use of annular objectives for angle gating," Appl. Opt., vol. 37, no. 22. pp. 5320-5326, 1998]. These methods are limited in terms of the resolution-to-field of view (FOV) trade-off where higher resolution decreases the field of view. Also, using a lens-based system always necessitates the object and image planes to be within a specific spatial arrangement (dependent on the focal length of the lenses used). For microscopy to obtain high resolution images, the NA of the objective has to be as high as possible leading to lower field of views. For lens-based applications, high NA and high resolution decreases the depth of imaging field (imaging volume) and the imaging plane is usually flat.

There is a need for a deep interrogation system of an object in turbid media without the drawbacks of the prior art.

There is also a need for a deep interrogation system and method with resolution to be at least 1-2 orders of magnitude better than DOT (tens of microns-microns) while facilitating higher endogenous contrast since we use the visible range of the spectrum.

There is also a need for a deep interrogation system and method of forming images with minimal or no processing required compared to DOT computational reconstruction to form real time or close to real time images.

There is also a need for a deep interrogation system and method of forming images without scanning requirements versus if multiple source detector configurations are not used for DOT, then mechanical scanning is required for this method to form images thus significantly hampering the stability of the measurements.

There is also a need for a deep interrogation system which is able to exploit a fiber optic plate or bundle, as manufacturing of optical fibers may be produced to the diameter to less than a micron, providing flexible light guidance and collection, allowing for bending of the imaging assembly when dealing in space constrained settings, for instance with small bioreactors, pharmaceutical product manufacturing or biological media.

There is also a need for a snapshot fiber-based approach for real time imaging requiring no mechanical scanning to acquire a snapshot or video capture of the area of interest.

There is also a need for an imaging sensing system and method which may be scaled to any size as without a lens on a distal end, and with little or no restrictions on spatial arrangement.

There is also a need for an imaging system and method with a NA which allows for a relatively higher resolution for larger field of views when compared to microscopy.

SUMMARY

According to one aspect, there is provided an imaging sensing system comprising:
i) a fibre optic plate (FOP) comprises a proximal end, a distal end and a body situated between said proximal and distal ends:
ii) at least one illumination component proximate said FOP, for illuminating an object; and
iii) an image sensor proximate said FOP, for sensing an image of said object, preferably said image sensor is a camera.

In one alternative, said image sensor is from about 0.6 to about 50 microns from said proximal end of said FOP. Said FOP may be constructed in any way providing core-cladding refracting index mismatch and guiding the light that enters from a sample side and reaches said image sensor. In yet another alternative, said image sensor is from about 0.6 to about 10 microns from said proximal end of said FOP. In one alternative, said FOP further comprises at least one optical fibre, preferably a plurality of optical fibres, each optical fibre having a first optical fibre end and a second optical fibre end, arranged longitudinally along the body of said FOP allowing for the transmission of an image from the distal end to the proximal end of said FOP to the other end of said FOP and to said image sensor, more preferably said plurality of optical fibres are bundled together, forming a fibre optical bundle or fibre matrix, such that each first end and each second end of said plurality of bundled optical fibres form a grid.

In one alternative, said grid is such that each end of each optical fibre is axially aligned with each adjacent optical fibre end forming a rectangular fibre optical bundle.

In another alternative, said grid is such that each end of each optical fibre is axially offset with each other forming a staggered fibre optical bundle.

In yet another alternative, said imaging system further comprises an illumination component.

In one alternative, said illumination component forms part of the FOP. In another alternative, said illumination component is separate said FOP.

In yet another alternative, said fibre optical bundle further comprises at least one illumination fibre, preferably a plurality of illumination fibres, proximate at least one optical fibre.

In one alternative, said fibre optical bundle further comprises at least one illumination fibre running along the length of said FOP and proximate at least one optical fibre. In a preferred alternative, said fibre optical bundle comprises an illumination fibre running along the length of said FOP and between at least two optical fibres of said FOP.

In another alternative, said at least one illumination fibre may run less than the length of said FOP. In yet another alternative, said at least one illumination fibre may run more than the length of said FOP.

In one alternative, each of said at least one illumination fibre is controllable allowing light transmission to be turned on or off, individually or as a whole.

In one alternative, said illumination component operates as a continuous wave illumination source. In another alternative, said illumination component operates as a pulse mode illumination source.

In one alternative, said illumination fibre operates as a continuous wave illumination source. In another alternative, said illumination fibre operates as a pulse mode illumination source.

In one alternative, said FOP has a pixel size from about 0.6 to about 100 microns. In a preferred alternative, said FOP has a pixel size of about 2-3 microns.

In one alternative, said FOP has a Numerical Aperture (NA) from about 0.0001 to about 0.4 In another alternative from about 0.001 to about 0.4. In a preferred alternative, said FOP has a NA less than or equal to about 0.15. In yet another preferred alternative, said FOP has a NA less than or equal to about 0.1 In one alternative, said FOP has a cross sectional shape selected from the group consisting of round, square and rectangular. In one alternative, said FOP has dimensions of at least 500 microns×500 microns. In a preferred alternative, said FOP has dimensions of about 3 mm×3 mm and a diameter of about 3 mm. In yet another alternative, said FOP has a length less than about 20 mm for NA less than 0.1. In yet another alternative, said FOP has a length of at least 20 mm with NA greater than 0.1. In another alternative, said FOP further comprises cladding, preferably light absorbing cladding. In a preferred alternative, said absorbing cladding is extramural light absorption cladding.

In yet another alternative, said imaging sensing system further comprises a refractive index matching zone between said FOP and said image sensor to reduce any impact of a gap (such as an air gap) between the FOP and the image sensor creating a refractive index mismatch and thus reduction of light guide-image sensor coupling. In a preferred alternative, said refractive index matching zone has a refractive index in the range of from about 1.4 to about 1.6. In a preferred alternative, said refractive index matching zone has a refractive index in the range of 1.5 In a preferred alternative, said refractive index matching zone is a refractive matching media, preferably a gel or refraction index matching glue.

In another alternative, said image sensor is a camera. In one alternative, said camera has no lens.

In yet another alternative, said camera has a lens. The camera further comprises an infrared protective barrier between said camera and said lens.

In one alternative, said image sensor has a pixel size of from 0.6 micron to about 100 microns. In a preferred alternative, said image sensor has a pixel size of about 1 micron.

In one alternative, said image sensor comprises a sensor type selected from Charge Coupled Device (CCD). Complementary metal-oxide-semiconductor (CMOS) and combinations thereof. Ina preferred alternative, said sensor type is CMOS, more preferably a CMOS camera. In one alternative, said image sensor senses from the group consisting of colour, spectral band or monochrome and combinations thereof. In a preferred alternative said image sensor senses monochrome. In one alternative, said combination comprises a narrow band light and a colour sensor, which creates a faux monochrome effect. In one alternative, said image sensor comprises a number of pixels of from about 100. In one alternative said image sensor comprises a number of pixels of from about 100 to about 10,000,000. In one alternative, to about 8,000,000. In yet another alternative, about 1,000,000, preferably about 100,000. In one alternative, said image sensor further comprises a dynamic range, which may further comprise hardware and software high dynamic range (HDR)/extended dynamic range (XDR). Industry standard dynamic range in cameras is limited to 8 to 12 bits, which limit the image contrast in scenes where bright and dark regions are imaged simultaneously. For e.g., the full range of bright to dark is divided into 0-255 unique values for an 8 bit camera and 0-1023 for a 10 bit camera and 0-4095 for a 12 bit camera. For brightly lit areas, the full capacity of the camera (corresponding to a 255 or 1023 level) is reached well before the dark regions can be imaged. This leads to an oversaturation effect where surrounding areas near a saturated pixel experience overflow resulting in no contrast when trying to properly expose the darker regions. To remedy this, a concept of extended dynamic range/high dynamic range (XDR/HDR) has been introduced whereby a higher/extended dynamic range can be obtained through a limited dynamic range of 8/10 bits. This process can be hardware or software mediated where a camera with HDR/XDR hardware can produce such images without needing any software mediation or a camera without such hardware can use software which allows to form HDR/XDR images after post processing of images acquired at different exposure levels. In one alternative, said image sensor further comprises a variable hardware pixel binning. In one alternative, said image sensor further comprises a variable frame per second (FPS) rate greater than 0 In one alternative a variable FPS rate greater than 0 to about 1000. In a preferred alternative, said FPS is about 100. In yet another alternative, said image sensor further comprises chip protection selected from an infra-red filter, protective glass and combinations thereof. In yet another alternative, said image sensor does not comprise chip protection selected from an infra-red filter or protective glass. In yet another alternative, said image sensor comprises the image sensor and processing electronics on one printed circuit board. In another alternative, said image sensor comprises the image sensor segregated from a main printed circuit board. In one alternative, the image of the desired object may be captured by the system via a reflectance mode of said system, wherein in reflectance mode, said FOP and illumination are situated on one side from the object of interest. In another alternative, the image of the desired object may be captured by the system via a transmission mode of said system, wherein in transmission mode, the desired object is situated between said FOP and said illumination.

In yet another alternative, there is provided an imaging sensing system wherein at least one NA reducer, in one alternative an aperture mask, to allow the use of a FOP having an NA greater than the said at least one NA reducer for angle gating. In one alterative, said at least on NA reducer having a NA of from about 0.0001-0.4 is placed, in one alternative on a distal end and in another alternative is placed on a proximal end of a FOP having a NA greater than or equal to the NA of said NA reducer, limiting the NA of said FOP. In yet another alternative said NA reducer is placed on both said distal end and said proximal end of said FOP. In another alternative, said FOP has a NA greater than the NA of said aperture mask.

In one alternative, said NA reducer comprises at least one optical fibre with a NA less than the NA of the FOP. In this alternative, said NA reducer comprising at least one optical fibre may be made of transparent optical material. In one alternative, any light passing through the NA reducer comprising at least one optical fibre is guided through the optical fibre by the principle of total internal reflection. In one alternative, the NA reducer comprising at least one optical fibre further comprises core and cladding material selected from the group consisting of silica glass, sapphire glass and a refractive index of said core and cladding is selected to achieve a desired NA value. In one alternative, the core may be hollow and the surrounding cladding may be silica. In yet another alternative, said NA reducer comprising at least one optical fibre is selected from photonic crystal fibre, hollow core fibre and combinations thereof.

In yet another alternative, said NA reducer comprises an aperture having an absorbing/non-reflective surface. In one alternative, the materials are selected from an absorbing polymer, silicon with an absorbing/non-reflective internal surface (in one example coated with carbon), a metal with an absorbing/non-reflective internal surface. In another alternative, said aperture may be a core comprising an optically transparent material. In one alternative, said optically transparent material is selected from silica glass, sapphire glass and combinations thereof. In this alternative, the optically transparent material is surround by an absorbing/non-reflective material as described herein. In this alternative (i.e. said core comprises an optically transparent material), unwanted particles, such as dirt or the like, is prevented from entering the system.

In yet another alternative, there is provided an imaging sensing system wherein an aperture mask with an aspect ratio defined as diameter:height of said aperture mask, resulting in a NA of from about 0.0001-0.4 is placed on a dital end of a FOP having a NA greater than or equal to the NA of said aperture mask for limiting the NA of said FOP. In another alternative, said FOP has a NA greater than the NA of said aperture mask.

In this application. "aperture mask" is defined as a device which restricts or reduces the NA. In a preferred alternative, said device is a mechanical device. In another alternative, the aperture mask is an optical FOP with a restricted NA, lower than the NA of the main FOP.

In one alternative, said aperture mask comprises a cap of a predetermined length with an aperture running along the length of said aperture mask.

In one alternative, said aperture running along the length of said aperture mask comprises a non-reflective surface.

In another alternative, said non-reflective surface runs the entire length of said aperture. According to yet another embodiment, there is provided a scanning fibre device comprising at least one optical fibre, preferably a single optical fibre combined with an electroreactive element in a casing, said single optical fibre and said electroreactive element connected to a detector. In one alternative, said casing is cladded.

In one alternative, said single optical fibre is centrally offset from a central longitudinal axis of said electroreactive element. In another alternative, said single optical fibre is centrally situated in relation to a central longitudinal axis of said electroreactive element. In one alternative, said electroreactive element is a piezoelectric tube.

According to yet another alternative, there is provided a lens based imaging sensing system with at least one positionally adjustable lens and iris unit within a detector housing. In another alternative, said iris comprises a central aperture that is adjustable in iris opening.

According to yet another alternative, there is provided a lens based imaging system with a plurality of positionally adjustable lens and iris units within a detector housing. Each of said plurality of positionally adjustable lens and iris units being positionally adjustable independent of each other.

According to yet another alternative, there is provided a human digit receiver in combination with the imaging sensing system described herein.

BRIEF DESCRIPTION OF THE FIGURES

FIG. 2 is an isometric and top view of a camera and FOP assembly;

FIG. 3B depicts various FOP arrangements:

FIG. 5 is a graph depicting contrast ratios of an image captured with the system for 0.17 NA FOP at various depths and various intralipid concentrations of Example 1;

FIG. 6 is a graph depicting contrast ratios of an image captured with the system for 0.25 NA with an objective lens at various depths and various intralipid concentrations of Example 1;

FIG. 11 depicts a scanning fibre mechanism, according to one alternative:

FIG. 12A depicts a lens based imaging sensing system with positionally adjustable lens and iris units, according to one alternative:

DETAILED DESCRIPTION

Figure 1B:
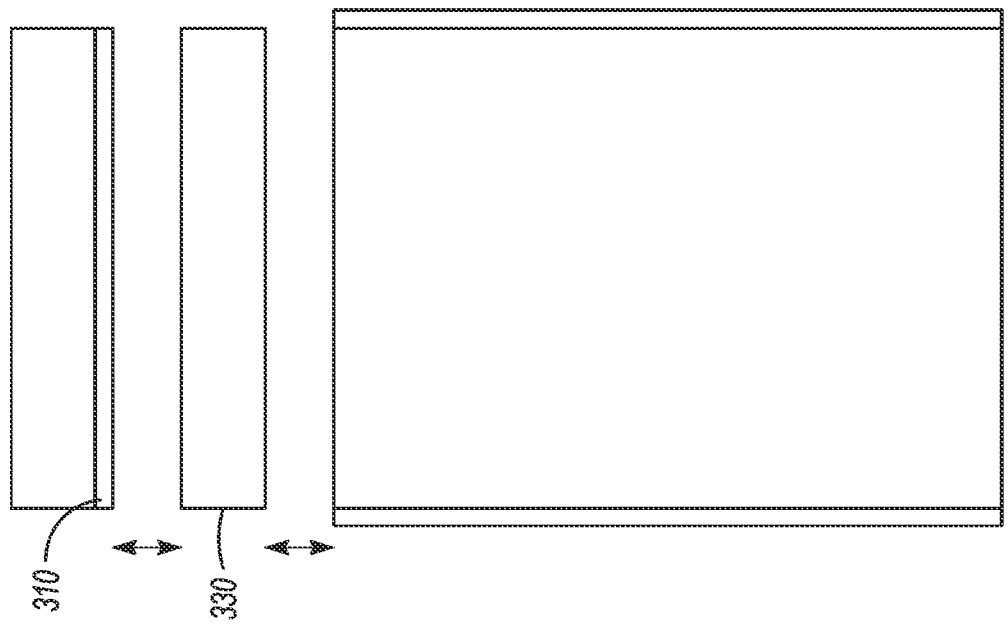
FIG. 1B is a longitudinal cross view of the imaging system according to one 30 alternative with a proximal end (facing the camera) lens.
Figure 1A:
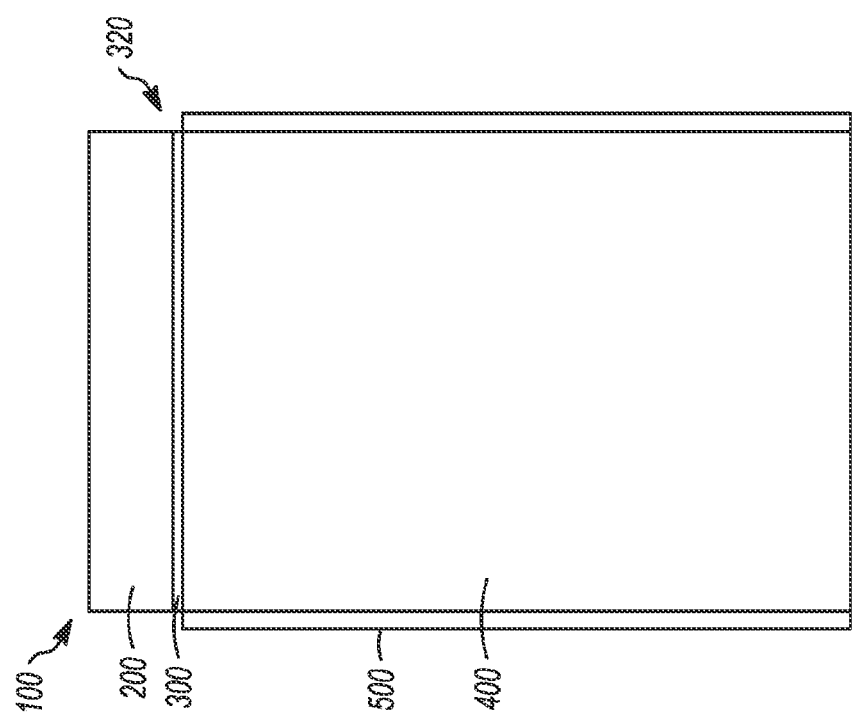
FIG. 1A is a longitudinal cross view of the imaging system according to one alternative without a lens.

Referring now to FIG. 1A, a cross-sectional view of the imaging system 100 according to one alternative is depicted. The imaging system comprising a camera 200, in this case a CCD/CMOS, an intermediate section 300 between the camera 200 and a fibre optic plate (FOP) 400.

When the imaging system 100 comprises a camera 200 without a lens, the intermediate section 300 is a refractive index matching section 320 which may be a refractive index matching gel.

Here the CCD/CMOS is coupled to the FOP directly using either a refractive index matching gel or a protective glass cover and a lens assembly (FIG. 1B) When the imaging system 100 comprises a camera with a lens, there is no need for any refractive index matching but rather the intermediate section 300 may comprise a combination of a protective glass cover (such as an infra-red window) to protect the lens and a lens assembly 330 (see FIG. 1B).

The camera 200 serves to convert the optical signal (light intensity) into a digital signal (digital pixel values) for analysis. The refractive index matching section 300 between the camera 200 and fibre optic plate 400 serves to reduce intensity loss at the interface of fiber optic plate and camera as well as it conditions the light rays entering the image pixels in the camera reducing the amount of inter pixel crosstalk. The FOP 400 serves as a gated conduit to allow filtering of diffusely scattered light intensity from the sample. This filtering is essential to perform subsurface imaging with better contrast when compared to conventional imaging techniques.

FIG. 1B also provides the lens 330 to camera 200 and lens 330 to FOP 400 distance dictated by the focal length of the lens 330.

The periphery of the FOP 400 comprises illumination fibers 500 (See FIG. 1A) running along the length of the FOP 400. The illumination fibers 500 provide illumination to the object of interest.

Referring now to FIG. 2, there is depicted an isometric and top view of two alternatives of the imaging system 100 wherein the detector is a camera 200. One depicting a cylindrical shaped FOP 400 with a round end and illumination fibers 500 running along the outside surface of the FOP 400 and the other depicting a cuboid shaped FOP 410 with a square end and illumination fibers 500 running along the outside of the FOP 400. The different shaped FOPs allow different illumination geometries for better subsurface imaging capabilities. Peripheral illumination and intertwined illumination allow for different spacing between the illuminating fibers and the collection fibers. This in turn results in better capabilities of resolving the photons that have higher probability of undergoing fewer light scattering events maintaining spatial integrity and overcoming diffusion.

Figure 3A:
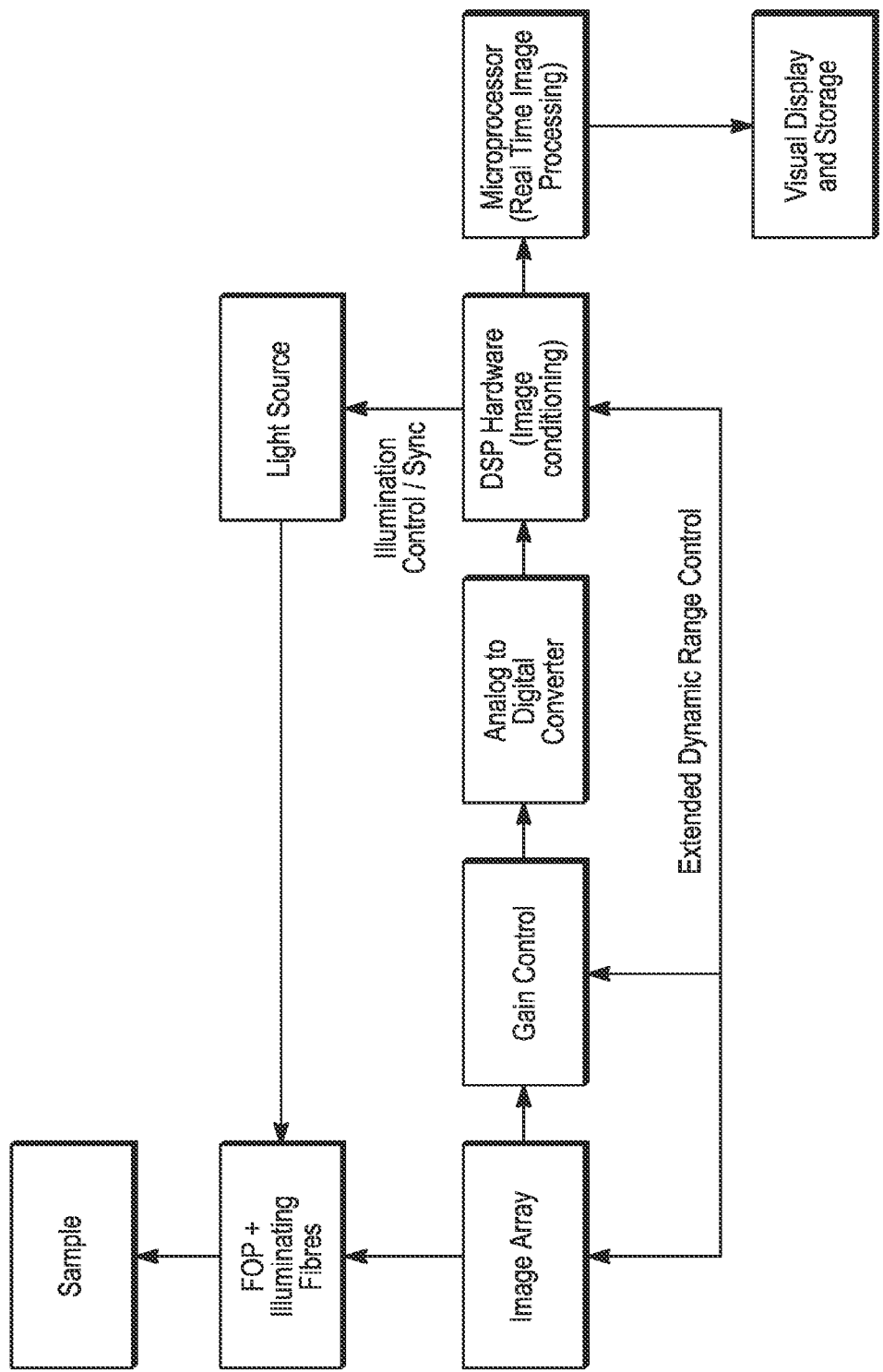
FIG. 3A depicts a schematic of a typical setup of the system according to one alternative.

Referring now to FIG. 3A, there is depicted a typical setup of the imaging system according to one alternative. A sample is placed in contact with the FOP and Illumination assembly. The light penetrates into the sample via diffusion and the light scattered back is collected via numerical aperture gated FOPs. The collected light is then relayed onto an image sensor array which is either directly coupled to the image sensor array using a refractive index matching gel or lens coupled to the image sensor array using a lens assembly. The raw pixel values from the image array is read out using the digital signal processing (DSP) hardware with extended dynamic range control. The raw analog signal is amplified using gain control and converted into digital data which is then fed into a DSP chip for image conditioning. The DSP hardware also allows to control the light source responsible for illuminating the illumination assembly. This allows multiple modes of operation such as continuous wave (CW), pulsed wave (PW) and hyperspectral (HS) illumination protocols. The conditioned image array is then passed onto a microprocessor which allows for real time image processing and the image is then presented on a display and stored for later use.

FIG. 3B depicts various arrangements of FOP. For FOP packing. FOPs may be fabricated in rectangular/square or hexagonal packing of unit fibers. The rectangular/square packing is beneficial when the size of each pixel is close to the diameter of the unit fiber. One-to-one matching can be achieved, increasing contrast of the transferred image. Hexagonal packing is best suited when the size of each camera pixel is at least two-three times smaller than the size of the unit fiber. Hexagonal packing offers packing efficiency (~90% vs ~78% for square packing). Irrespective of the packing, the final FOPs may be fabricated in any shape feasible.

Illumination Arrangement

Although peripheral illumination may be practical and facile to achieve, due to the varying distance of the unit fibers from the peripheral illumination fibers, there is a gradient in the light intensity that decreases exponentially as one moves towards the center of the FOP which limits the extent of the FOP and provides uneven illumination. Despite the drawbacks, the peripheral illumination may be used efficiently to perform subsurface imaging.

Intertwined illumination, provides a more balanced light distribution across the field of view. This type of arrangement may be used to create FOPs with large extents allowing to image larger areas simultaneously. Moreover, selective illumination of fibers can be done to achieve another layer of gating on top of the gating achieved through FOPs. It further allows for variable distance between illumination fibers and detector fibers which may be used to filter highly diffuse photons from less scattered photons.

As discussed above, continuous wave (CW) illumination source is light delivered continuously to the sample. Pulse wave (PW) illumination source is light delivered in a pulsed form ranging from picoseconds to milliseconds of pulse duration.

In one alternative, switching illumination. i.e. from PW to CW illumination and vice versa, may be used while turning singular fibers or a combination of fibers on and off selectively.

EXAMPLE 1

1.1 Numerical Aperture Gated Imaging Device

Figure 3D:
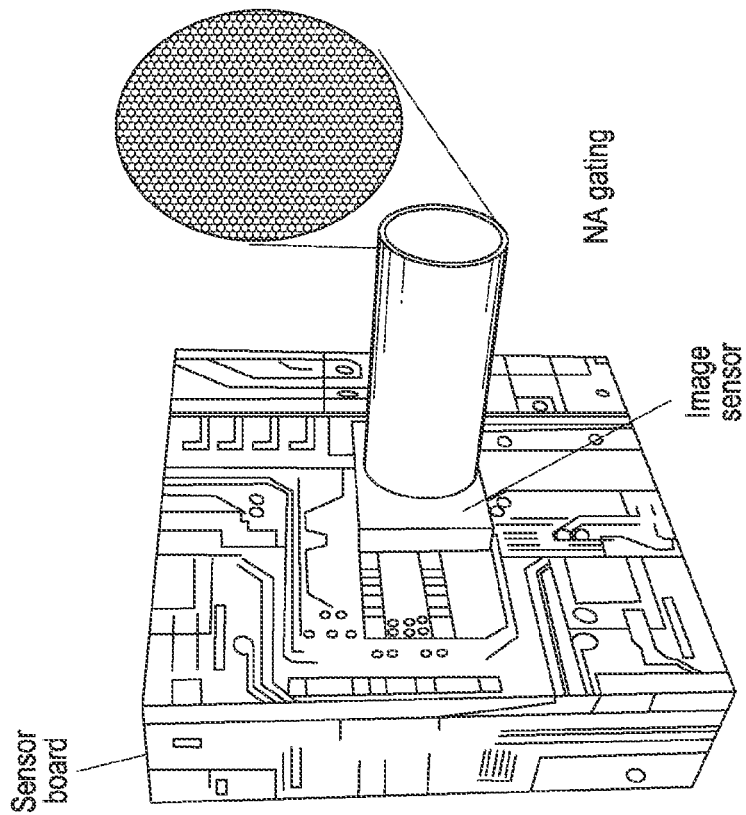
FIG. 3C depicts the experimental setup for Example 1 and FIG. 3D depicts the FOP for Example 1.
Figure 3C:
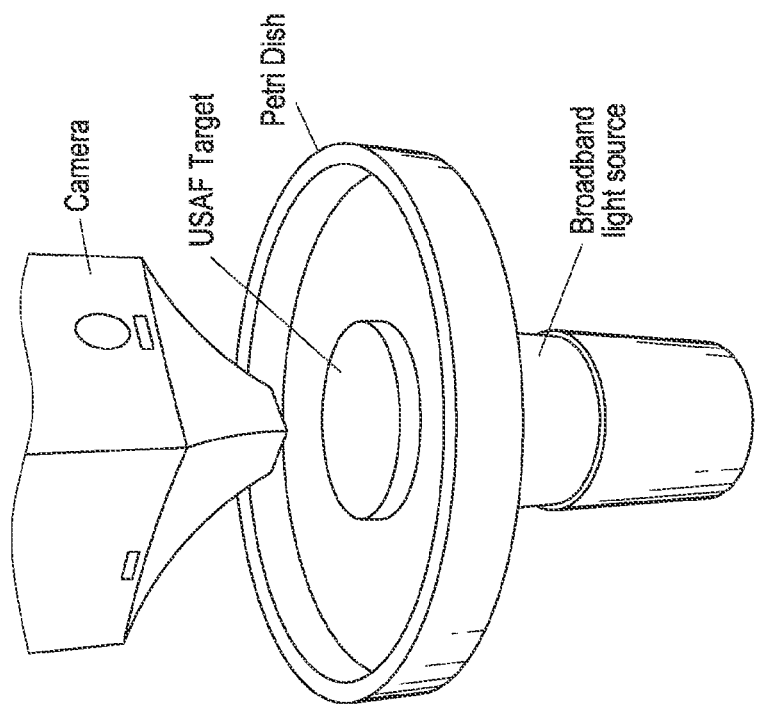

Referring now to FIGS. 3C and 3D. A Raspberry Pi camera module v2 (Sony IMX219 8-megapixel sensor) was custom fitted with FOPs ((1) 0.55NA FOP, 13 µm core, 3.2 mm diameter, Schott, USA and (2) 0.17NA, 15 µm core, 3.6 mm square, Collimated Holes, USA) after removal of the cover glass/filter protecting the sensor surface. A broadband light source was used to project light onto a transparent petri-dish with a USAF target glued to the bottom. The FOP camera was translated in the Z-direction with a resolution of 100 µm in the range of 0-2 mm. FIG. 3D shows the FOP camera coupled directly to the exposed sensor surface. The proximal surface of the FOP was placed in contact with the surface of the image sensor using mineral oil (Life, Canada n~1.46~1.47) to reduce the refractive index mismatch between both the surfaces. A custom 3D printed case was designed to hold the assembly firmly in place. The distal surface of the FOP was used as the imaging inlet to allow conduction of light from the sample surface to the image sensor. The numerical aperture prescribed by the refractive index mismatch of the core and cladding of the FOPs (0.55 and 0.17) was responsible for numerical aperture gating. A 1951 USAF target was used as a test sample and was imaged using two FOP based camera setups and a lens based camera (Microscope objective, 0.25NA Motic. China) setup. To emulate a scattering environment, varying concentrations (1-4%, mimicking low and the high range of scattering in human tissues—µs' (1-4 mm-1)[H. Assadi. R Karshafian, and A. Douplik, "Optical scattering properties of intralipid phantom in presence of encapsulated microbubbles," *Int. J. Photoenergy*, vol. 2014, no. 471764, 2014], [S. L. Jacques, "Optical properties of biological tissues: a review," *Phys. Med Biol.*, vol. 58, no. 11, pp. R37-61, 2013]) of Intralipid (Sigma Aldrich, USA) was used in a Petri dish. The USAF target was immersed inside the Intralipid and the camera was placed on a 3D translation stage. Zero imaging depth was considered to be at the point when the distal end of the FOP was in direct contact with the surface of the target and the Petri dish was filled out by Intralipid. The FOP camera was translated incrementally upwards by 100 µm steps increasing the layer of Intralipid between the distal end of the FOP and the target. For lens based setup, a square plunger was designed with a window made of silica microscopic cover slip. Zero imaging depth for this setup was considered when the cover slip was in direct contact with the target and the lens was focused onto it. The plunger was translated with increment of 100 µm similar to the above described setup. The translation was continued until the distance between the target and the distal end of the FOP surface/cover slip was 2 mm. A collimated LED light source (MCWHL5, Thorlabs, USA) was used to illuminate the target from the bottom within the framework of the trans-illumination geometry. Group 3 element 3 (~50 µm size of the grooves) of the 1951 USAF target was chosen as a region of interest for all three setups.

1.2 Image Processing

Due to the non-uniform illumination conditions and hexagonal arrangement of cores inherent in the design of the FOP camera, the image acquired would always have a variable background and presence of repetitive cladding pattern. Hence, a background correction needs to be performed to improve the image quality. This was achieved by using a differential method where two Fourier filters were employed to estimate the background/cladding pattern and to suppress the high frequency noise. The filter created was a low-pass Butterworth filter as described below [Rice University. "2D Frequency Domain Filtering and the 2D DFT," MATLAB Code. [Online]. Available: https://www.clear.rice.edu/elec301/Projects01/image_filt/matlab.html].

$$f(u,v) = \frac{1}{1 + \left(\frac{r(u,v)}{\text{cutoff}}\right)^{2*n}}$$

where u, v, represent the spatial frequency components, cut-off was used to define a normalized radial extent from the origin and n represents the order of the filter and r is the radial distance from the origin in the frequency domain. The cut-off was manually selected to obtain a background intensity variation and for reducing the high frequency components (noise) and it ranged from 0.001-0.008 for filter 1 and 0.03-0.08 for filter 2. For all image processing, a first order filter was used as it performed adequately without introducing artefacts.

1.3 Contrast Ratio

Figure 4A:
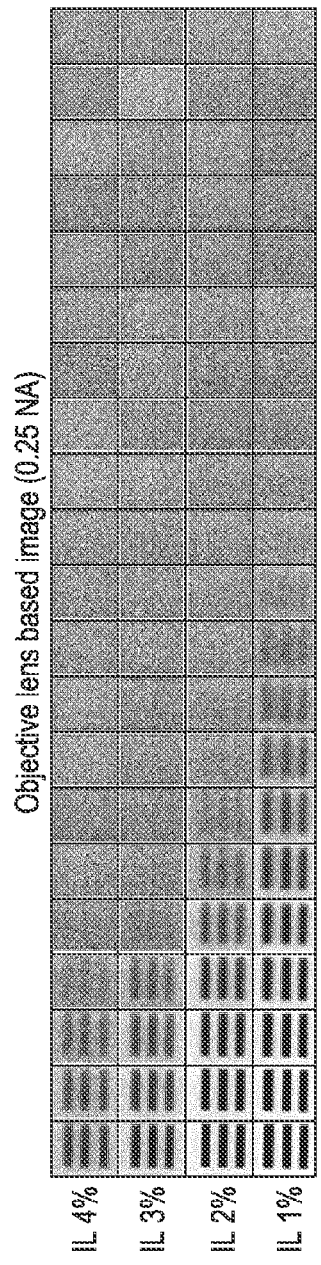
FIGS. 4A, 4B and 4C are a series of images acquired with the current system at various NAs of Example 1.
Figure 4B:
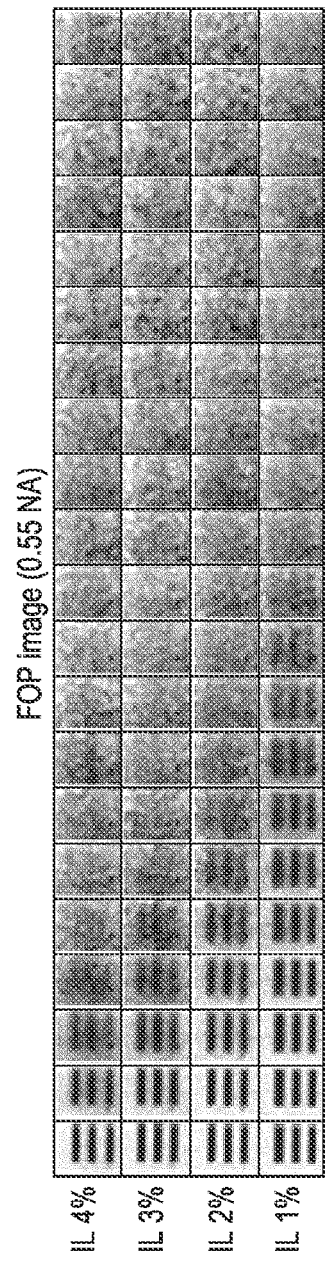
Figure 4C:
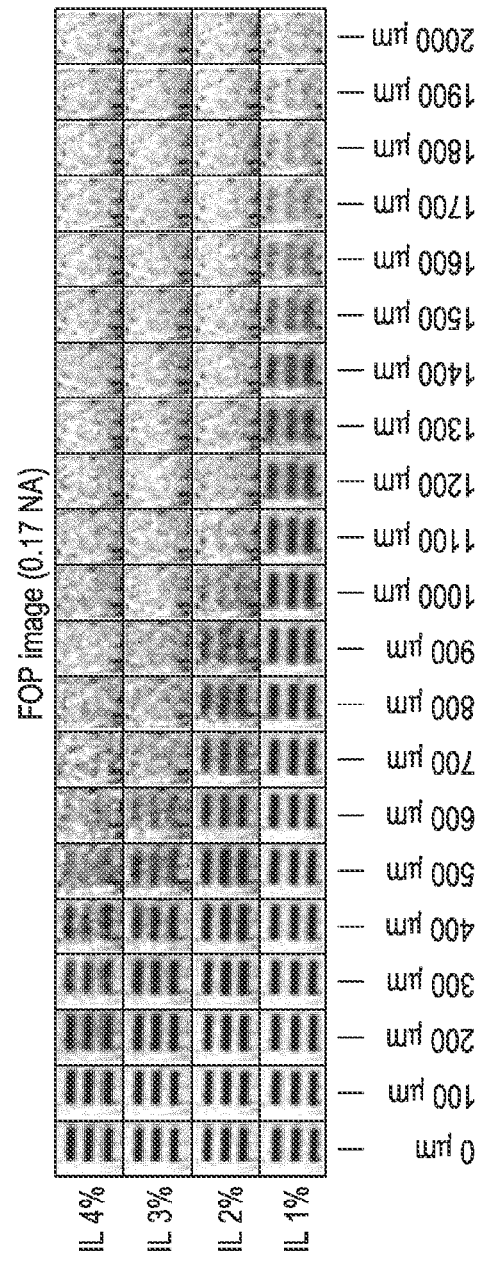

In order to characterize the imaging depth, a contrast ratio was calculated for each image. Two regions (3×3 pixels) were selected inside the image where the target was located (the black lines in FIG. 4). A similar window was chosen for the background and the average intensity for both was calculated. The resultant contrast ratio was defined as $$\text{Contrast ratio} = \frac{I_{target} - I_{background}}{I_{target} + I_{background}}$$

Wherein I is defined as intensity A threshold of 10% was used to define as the imaging interrogating depth. The standard deviation of the image without the presence of any target was calculated and this value was found to be around 7% for FOP based images. Hence, 10% was chosen as a threshold to compare all the imaging setups. This value was used to compare imaging depths for all the setups.

2. Results and Discussion

Referring now to FIG. 4, a summary of images acquired through all the setups is shown. The rows represent increasing concentration of Intralipid from 1-4% and a comparison of 0.17NA FOP. 0.25NA lens and 0.55NA FOP is presented. The columns represent the depth of target immersed inside a scattering layer of Intralipid. The depth was controlled using a translation stage to change the distance between the distal surface of the FOP and the surface of the target.

A visual comparison of the images obtained through all the setups is provided in Referring now to Figure. The rows of images correspond to an increasing concentration of Intralipid. The 0.17 NA FOP (FIG. 4C) depicted in an increased imaging depth when compared to the other imaging setups. For 0.17 NA FOP, the visibility of the lines is lost around 1700-1800 µm compared to 1100-1200 µm for 0.25NA (FIG. 4A) lens and 800-900 µm for 1% Intralipid concentration. The objective images and 0.55NA (FIG. 4B) FOP images have similar imaging depths. All the images were processed using the method described in section 1.2 above.

Figure 7:
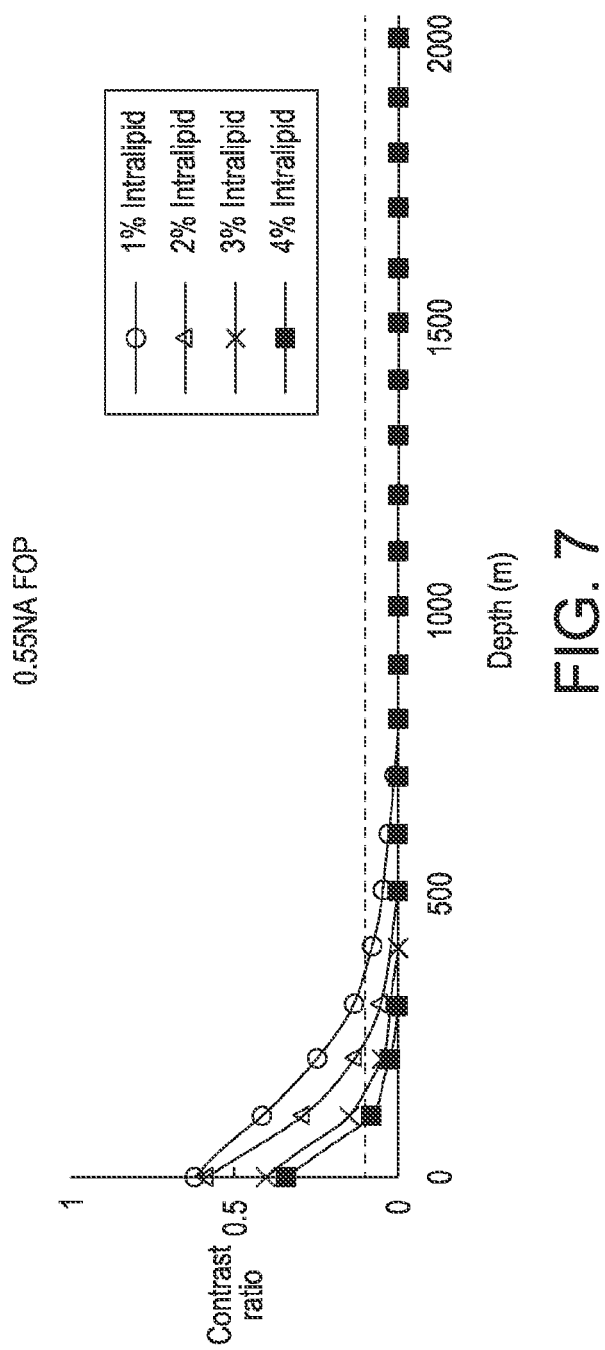
FIG. 7 is a graph depicting contrast ratios of an image captured with the system for 0.55 NA FOP at various depths and various intralipid concentrations of Example 1.
Figure 8:
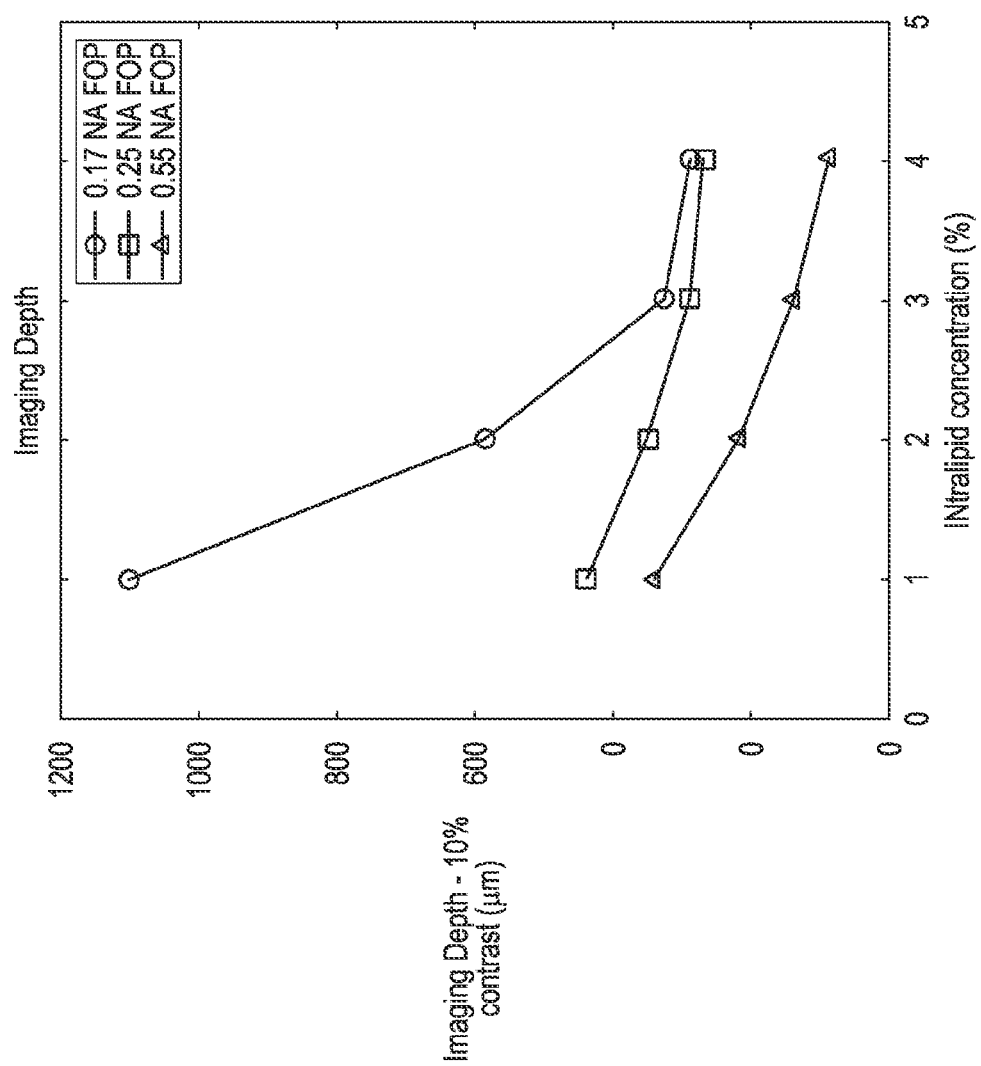
FIG. 8 is a graph depicting image depth with varying intralipid concentrations for 0.17 NA FOP, 0.55 NA FOP and 0.25 NA with an objective lens of Example 1.

FIG. 5 depicts the contrast ratio for 0.17NA FOP for various depths for various scattering media ranging from 1% intralipid to 4% intralipid. FIG. 6 depicts the contrast ratio for 0.25NA objective lens FOP for various depths for various scattering media ranging from 1% intralipid to 4% intralipid. FIG. 7 depicts the contrast ratio for 0.55NA FOP for various depths for various scattering images ranging from 1% intralipid to 4% intralipid FIG. 8 depicts the imaging interrogating depth at 10% contrast threshold for all the setups of imaging depth of different NA configurations for various scattering regimes.

A contrast ratio threshold of 10% (black dashed horizontal line—0.1 in FIG. 5-7) was chosen to compare the imaging depths for all the setups and the imaging depth at this ratio was considered to be the imaging depth of the camera assembly. The slope of contrast drop was gradual for 0.17 NA FOP compared to the other setups. This gradual decrease in slope corresponds to a greater imaging depth for low NA FOP when compared against a lens based setup as well as a higher NA FOP. FIG. 8 depicts the imaging depth at 10% contrast for all the setups at varying scattering parameters. For the lower scattering, the lower NA FOP performed considerably better at resolving the target at deeper locations. Reducing NA of the FOP also results in a substantial improvement in imaging interrogating depth but, the dependence of the imaging depth on NA proves to be non-linear. The imaging depth for 0.17 NA FOP for 1% Intralipid was around 1150 µm compared to 450 µm and 400 µm for 0.25NA lens and 0.55 NA FOP respectively, this corresponds to an approximate ratio of 3 for the lower scattering. This ratio decreases as the scattering increases and becomes closer to 1 for higher scattering conditions (4% Intralipid). This can be likely explained by the fact that the higher scattering results in an increased crosstalk between the optical fibers (highly diffuse photons are incident on the fiber at angles greater than the acceptance angles prescribed by the NA of the fiber) of the FOP as well as a chance of increased conduction of light through the cladding of the FOP. The resultant contrast is affected decreasing the quality of the image and thus the imaging interrogating depth. It was also observed that for the 0.55NA FOP, the contrast at zero imaging depth proved to be close to 0.5 when compared to the other setups where this contrast was close to 1. Due to the higher NA of this FOP, the crosstalk between the fibers is relatively large thus providing a reduced contrast even at zero imaging depths. Potentially, FOPs with extramural absorption can be utilized to minimize such cross talk and improve the imaging quality.

The reduction of NA leads to an imaging volume which is small enough to retain the spatial contrast but larger than a lens-based volume and facilitating better contrast than a lens based image, particularly in media with high light scattering. The above shows "lens-based" versus "lensless" comparison of images in samples with scattering properties comparable with human skin.

Figure 9:
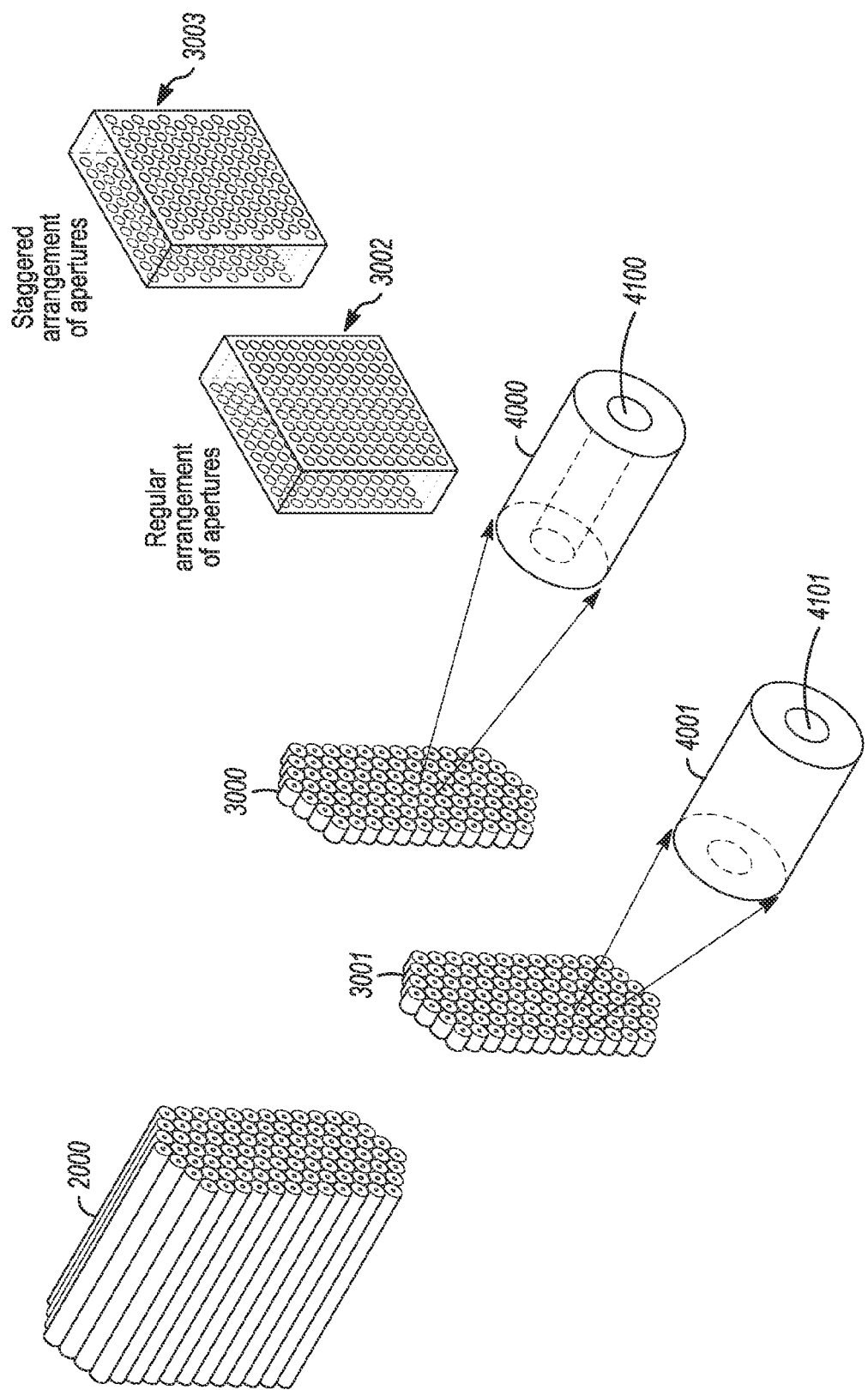
FIG. 9 is an exploded view of an imaging sensing system with a mechanical aperture mask and an optical aperture mask, according to one alternative.
Figure 9A:
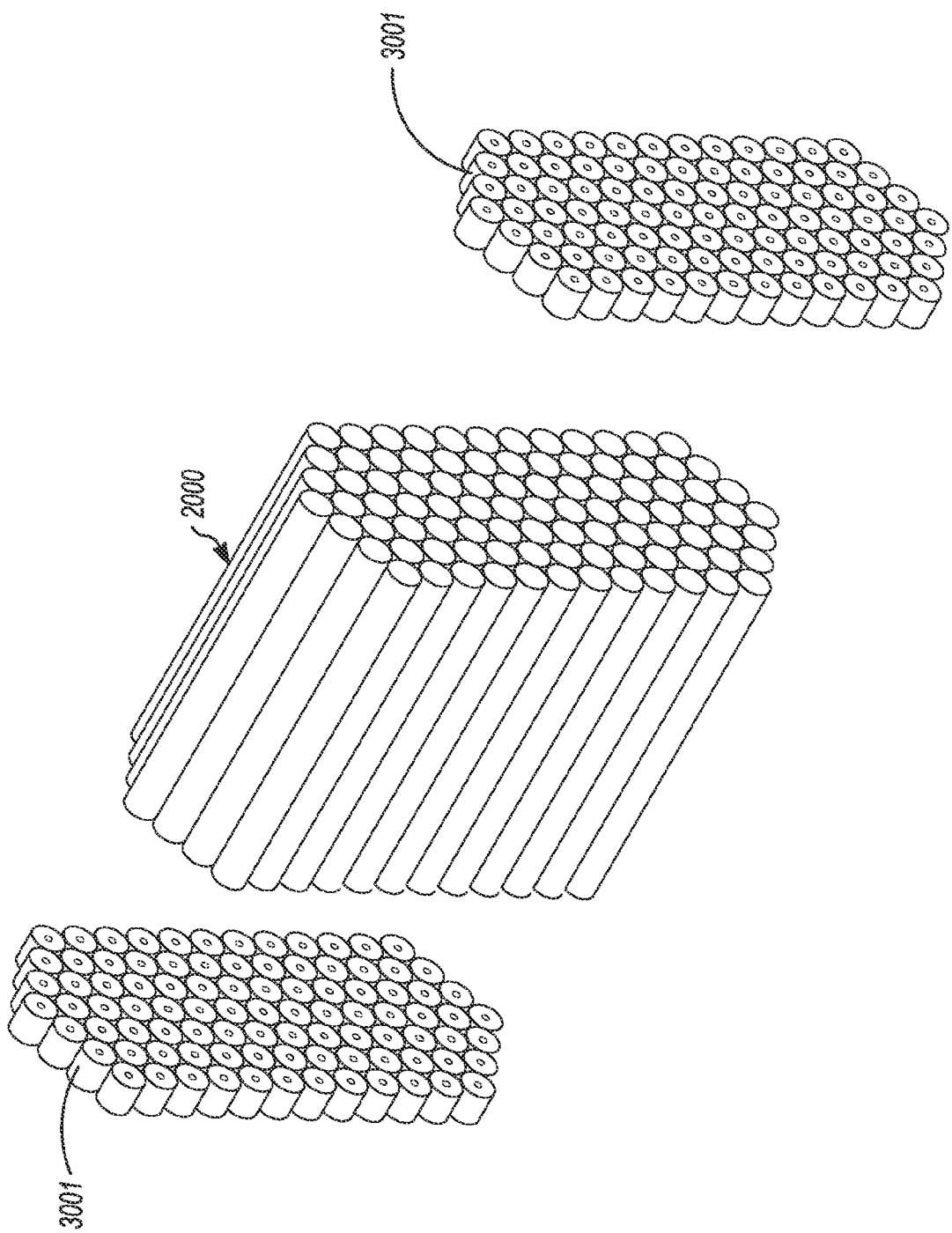
FIG. 9A depicts aperture masks at both the distal end and proximal end of a FOP, according to one alternative.

Referring now to FIG. 9, there is depicted an exploded view of a plurality of optic fibre aperture masks 3001 and non-optic fibre aperture masks 3000 on the ends of optic fibres 2000 forming a FOP. Each of said plurality of non-optic fibre aperture masks 3000 comprises an aperture mask cylinder cap 4000 with a centrally located aperture 4100 running the entire length of the aperture mask cylinder cap 4000. Also seen is an optic fibre aperture mask 3001 comprising a central core 4101 surrounded by cladding 4001. 3002 depicts a regular arrangement of aperture masks and 3003 depict a staggered arrangement of aperture masks. Referring now to FIG. 9A, there is depicted an exploded view of optic fibres 2000 forming a FOP with optic fibre masks 3001 situated at both the proximal and distal ends of the FOP. The optic fibre mask may also be situated only at one of the proximal or distal end of the FOP Non-optical fibre masks 3000 (not shown) may also be arranged similarly. The masks situated at the distal end is the primary NA gating unit which restricts the angle of light. The mask located at the proximal end allows for further light restriction exiting the FOP proximate the detector. This facilitates reduction of crosstalk between the imaging pixels further increasing the contrast in a synergistic manner (given there can be a finite distance between the FOP and sensor). In one alternative, the optical fibre mask may be an integral part of the FOP and manufactured with techniques such as, but not limited to, photolithography, 3D printing, structured coating (coating gun), cold additive manufacturing (requires metal base) and combinations thereof. The optical fibre mask may also be manufactured separated from the FOP and adhered to the FOP as described herein.

Figure 10B:
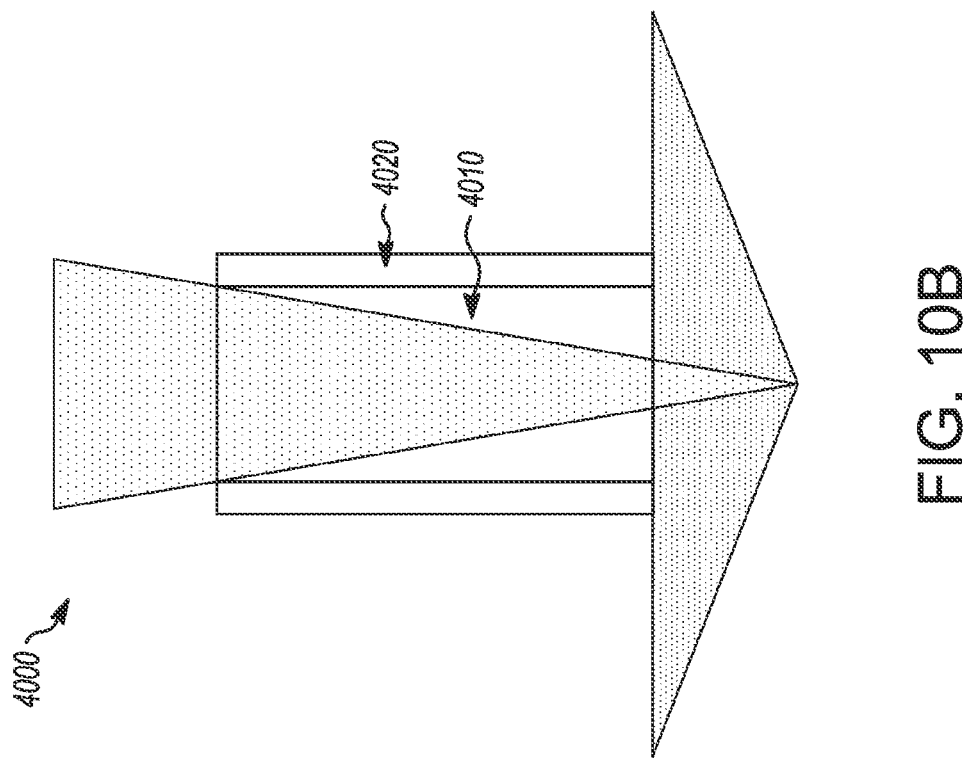
FIG. 10B depicts a mechanical aperture mask, according to one alternative.
Figure 10A:
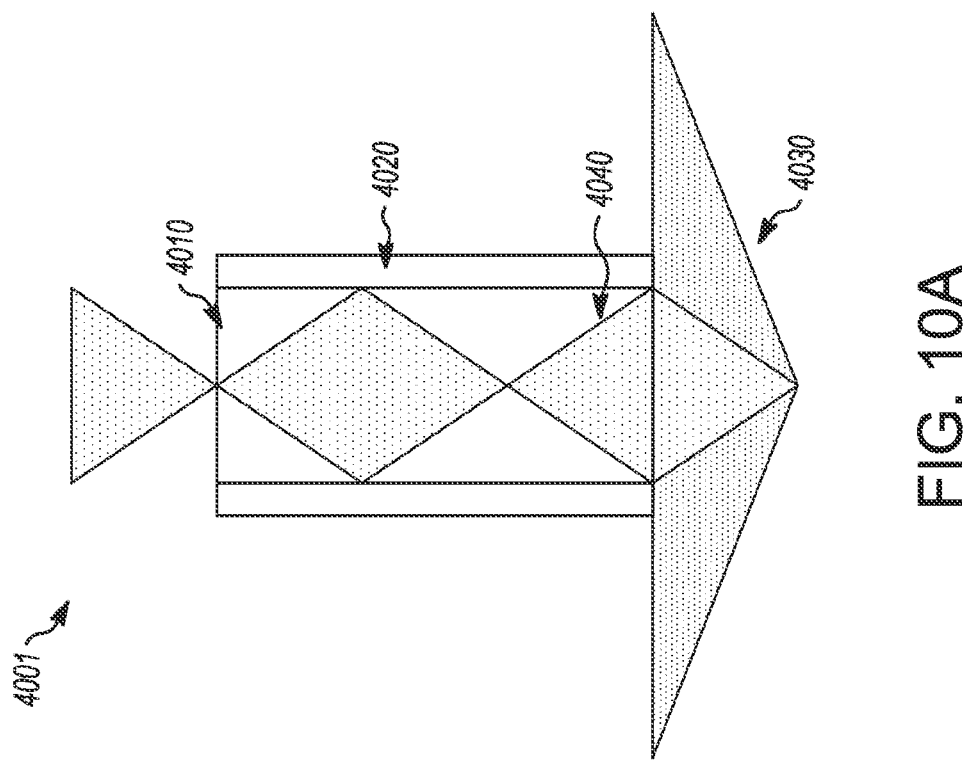
FIG. 10A depicts an optical fibre aperture mask, according to one alternative.

Referring now to FIG. 10, there is depicted a comparison of the system with a non-optical aperture mask FIG. 10B and with an optical fibre mask FIG. 10A In FIG. 10A, the NA of the fibre optic controls the light entering the optic fibre. Total internal light reflection occurs at the internal surface of the optic fibre (the interface between 4010 and 4020). Light reflects based on the refractive index mismatch of the central core 4010 and the cladding 4020, resulting in a guiding numerical aperture (NA) which restricts the angle of photons within the optic fibre. Light 4030 is scattered in all angles by the sample and the photons 4040 are restricted into the FOP based on the NA of the optic fibre. The optic fibre may be made from standard silica or other materials, such as sapphire, or the like, or materials known to those skilled in the art. The NA in this scenario is from about 0.0001 to about 0.4.

In FIG. 10B, the light passes through the aperture resulting in a guiding geometric cone which restricts the angle of the photons. Although light is scattered in all angles by the sample, the photons are restricted based on the aspect ratio (diameter:height) of the aperture mask resulting in an effective NA less than or equal to the NA of the fibre optic. This allows the use of commercially available fiber optics of NA outside the range of 0.0001 to about 0.4, preferably greater than 0.4.

The aperture mask may be adhered to the high NA FOP, preferably to the surface of the high NA FOP by using refractive index matching adhesive. In one alternative, said refractive index matching adhesive is selected from commercially available epoxy, ultra-violet (UV) curing resin and combinations thereof. In order to affect the adhesion of the aperture mask to the FOP, the aperture mask once aligned and placed on the end of the FOP with an adhesive may be cured under heat or UV light. The aperture masks may be made from silicon based materials, metallic materials and absorbing polymers through lithography techniques.

Referring now to FIG. 11, there is depicted a cut-away view of single fiber scanning mechanism comprising a single optical fibre 3300 within an electroreactive element, in this case a piezoelectric tube 2200, further encased in a housing or outer casing 1100 with a detector unit 4400 at one end thereof. The fibre 3300 is centrally offset, in this alternative to facilitate fabrication given a tube sized electroreactive element is used. The fibre 3300 may also be centered and not offset. The fibre 3300 scans a pre-set area in a pre-determined pattern to transfer light from the proximal end to the detector unit 4400. In this case, the optical fibre 3300 restricts the NA. The fiber scanning mechanism may comprise a single pixel detector or a pixel array detector.

Figure 12B:
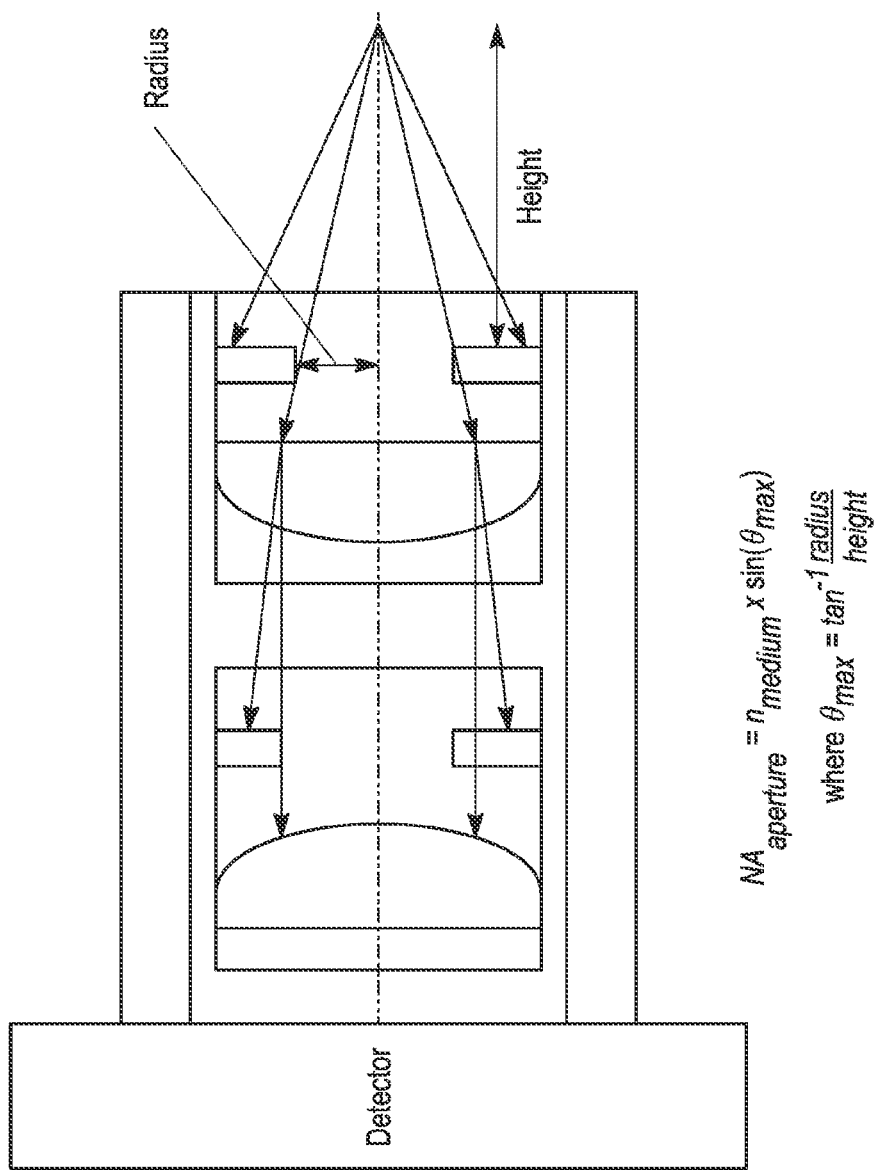
FIG. 12B depicts how the positionally adjustable lens and iris units control the entry of light to the detector, according to one alternative.

Referring now to FIGS. 12A, 12B. 13 and 14, there is depicted a lens based unit with lens and iris units comprised of alternating spaced apart axially aligned lenses 5200 and irises 5300. The lenses 520M and irises 5300 are housed in a cylindrical housing 5400 that is cladded and does not allow light to pass through the walls of the cylindrical housing 5400. The cylindrical housing 5400 leads to the detector 5100. In this instance, each pair of lens and iris unit is positionally adjustable in relation to each other along the length of the cylindrical housing 5400. This may be accomplished as understood by a person of ordinary skill in the art. One alternative is to have each pair movable along the length of the interior of the cylindrical housing 5400 via a threaded arrangement or through a sliding arrangement such as the ultra-think actuator family. The lenses may be single or multiple combinations of achromatic or aspherical or both achromatic and aspherical. Iris 1 and Ins 2 control the angle of photons reaching the detector allowing for angle gating allowing for non-contact adjustable angle gating of photons. FIG. 12B depicts how the lens and iris units perform the angle gating. The first iris reduces the angle of incoming photons due to the restricted size of the first ins. This first restricted photon angle passes through the first lens. The light diffracts around the edges of the $2^{nd}$ ins which causes a decreased image contrast because of unwanted light. The $2^{nd}$ iris further restricts this light from reaching the detector. The $2^{nd}$ ins may also provide secondary restriction of the angle of light reaching the detector.

Figure 13:
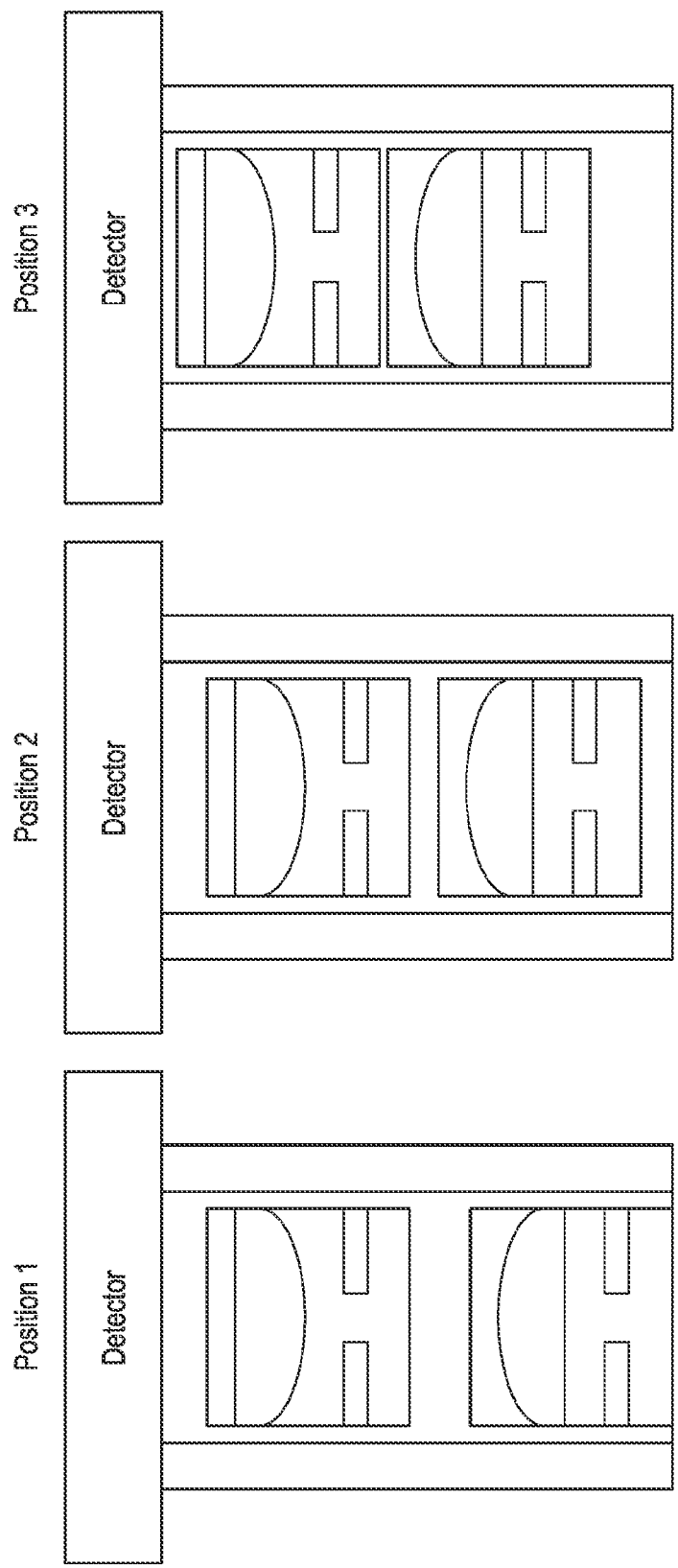
FIG. 13 depicts the system of FIG. 12 with each lens and iris unit in different positions, according to one alternative.

FIG. 13 depicts three different arrangements of lens and iris units separated at different distances. Each lens and iris unit being freely movable independent of each unit, within the housing and able to sit in any position therein depending on the specific situation. Position 1. Position 2 and Position 3 allow for various focus adjustment of the image by changing the position of the lens element.

Figure 14:
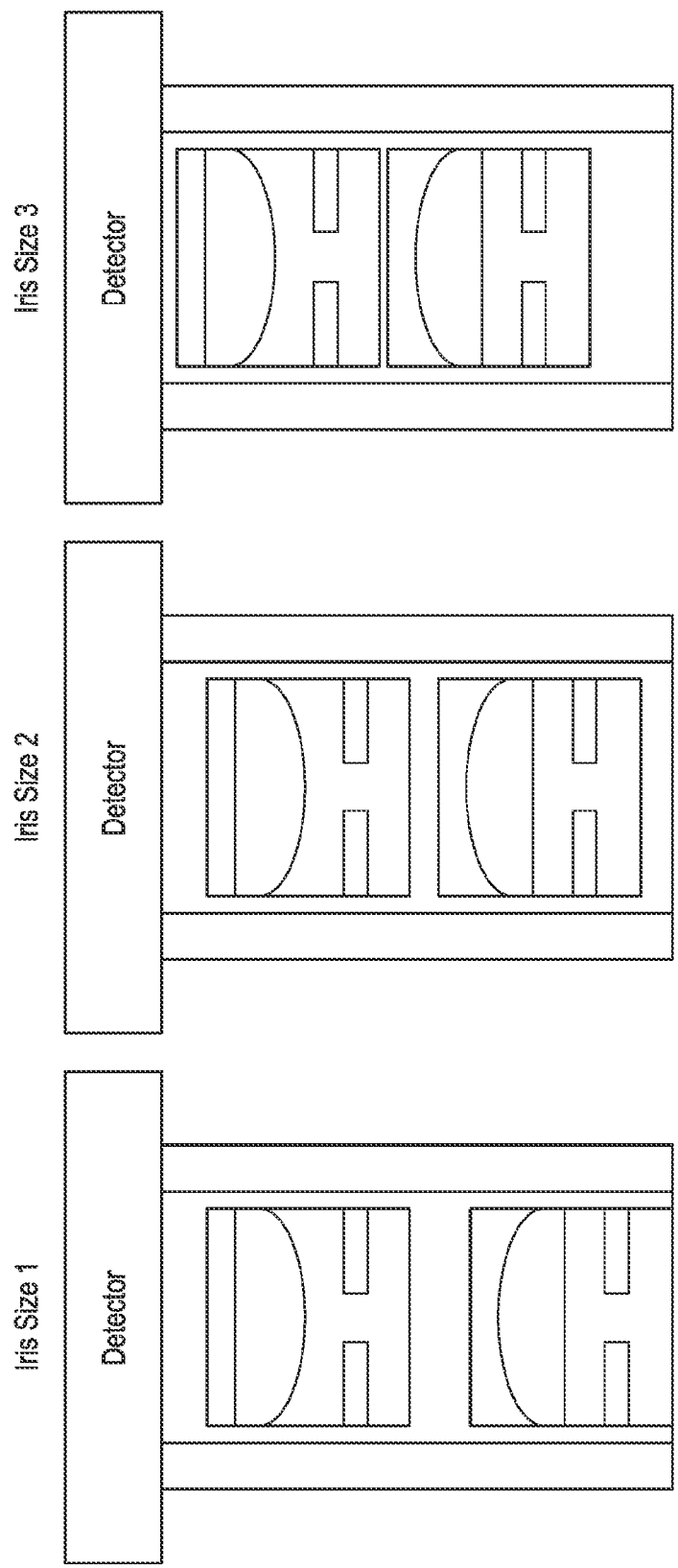
FIG. 14 depicts the system of FIG. 12 with each lens and iris unit in different positions with irises of varying diameters, according to one alternative.

FIG. 14 depicts three different positional arrangements wherein the irises are of different sizes. Each iris being adjustable independent of each other. Decreasing the size of the irises allow for low angle photons to reach the detector and vice-versa. Iris size 1 is suitable for a low angle restriction to filter out photons generally arriving at smaller angles, the proximal (to the detector) iris may also be narrower to further reduce stray light/diffracted light resulting in a lower angle of light reaching the detector. Iris size 2 is suitable for a synergistic effect of allowing low NA light reaching the detector Iris size 3 is suitable for allowing a high NA light to reach the detector. Multiple images at different irises may then be combined to forma higher contrast resulting image.

Figure 15:
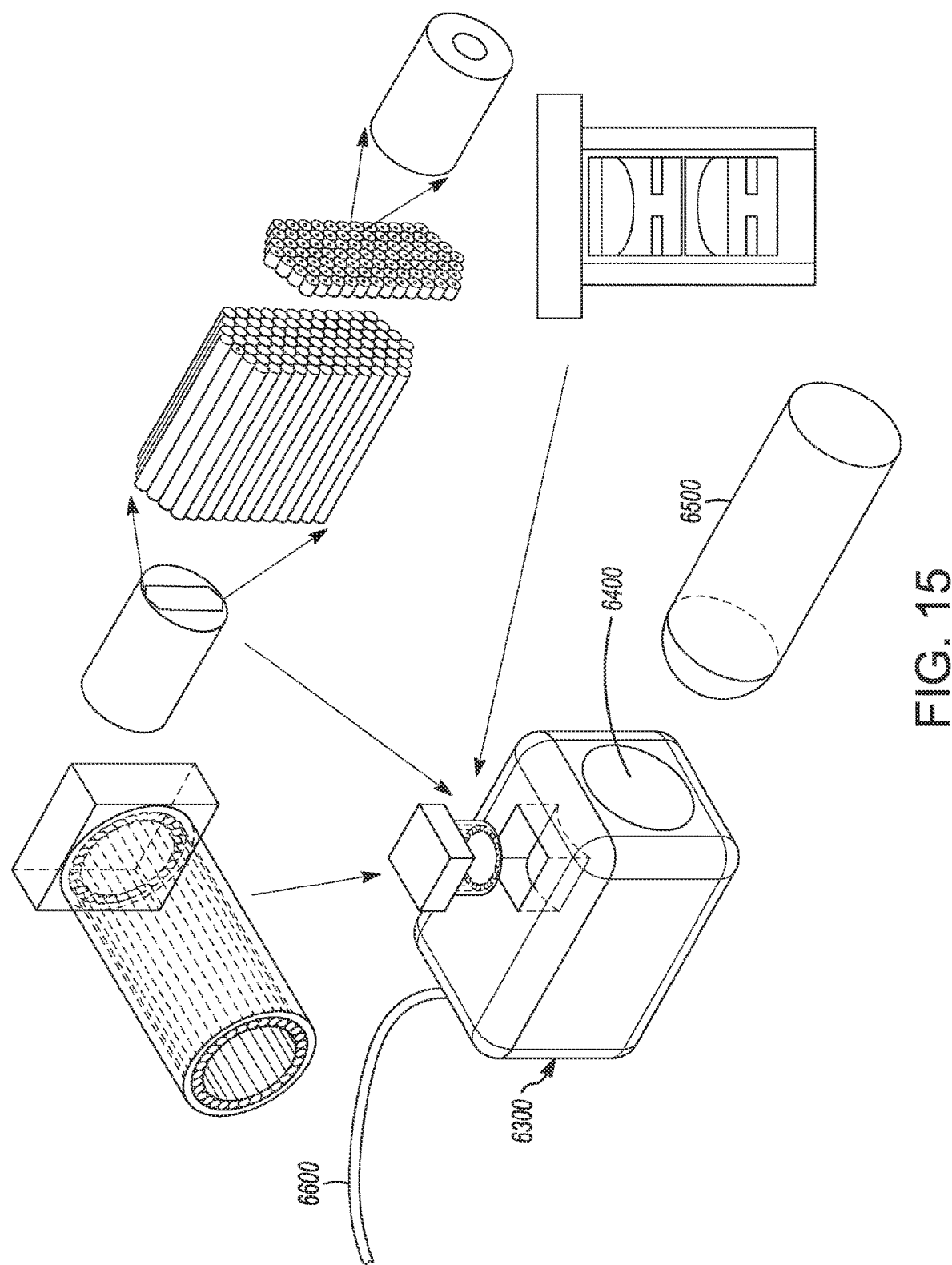
FIG. 15 depicts a human digit receiving unit in combination with the imaging sensing systems described herein.

FIG. 15 depicts the addition of a human digit receiver to allow imaging sensing of a human digit such as a finger or toe. The imaging sensor may be any of the sensors described herein and is attached to a human digit receiver, such as a spring loaded finger clip receiver 6300 with an opening 6400 to receive a finger or toe 6500. The system may be connected to a computer or the like by a cable 6600. The system may also be connected to a computer wirelessly. The image sensor is either attached to a FOP and illumination unit or an electronically adjustable lens unit with electronically adjustable apertures. The illumination unit has monochromatic, multi-spectral or hyperspectral illumination options and provides light for imaging skin of the finger or toe. In this particular example, the finger nailfold region. The FOP unit may be placed directly in contact with the skin of a finger or toe to perform numerical aperture gated imaging. The adjustable lens unit with apertures may be used with auto-focus mechanism to perform non-contact numerical aperture gated imaging. The adjustable lens unit with apertures may also be used with a manual focus mechanism.

EXAMPLE 2

Nailfold Capillaries Measurement

Figure 16A:
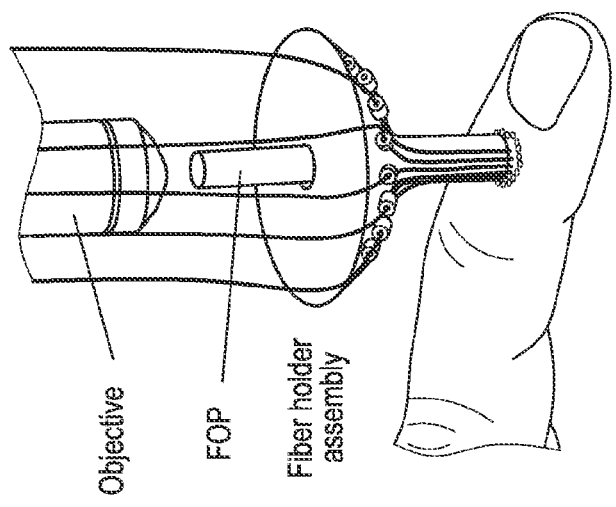
FIGS. 16A and 16B depict the system measuring capillaries of a finger and the resultant images, according to Example 2.
Figure 16B:
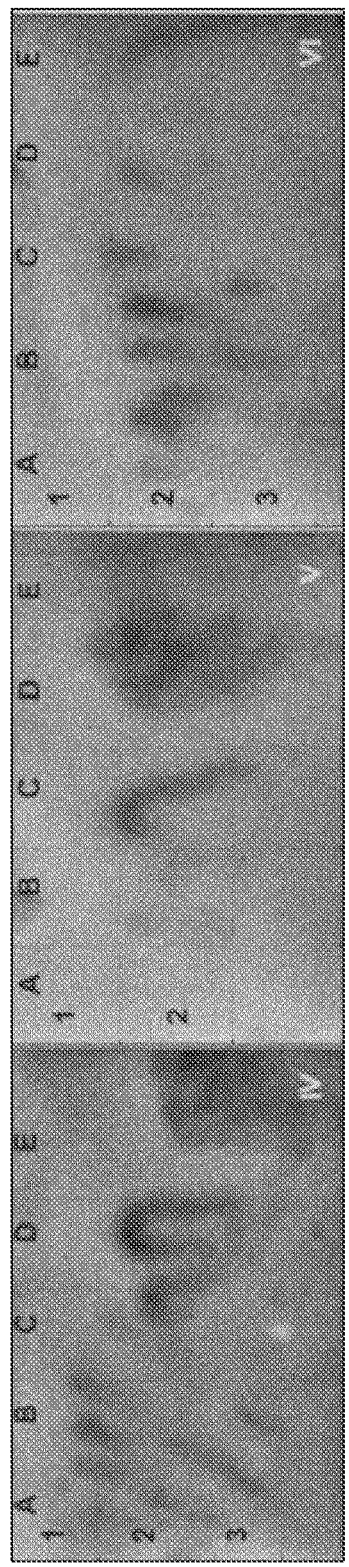

Referring now to FIGS. 16A and 16B, an imaging system inside an external holder used to guide light through illumination fibres along the periphery of the FOP. The FOP rests on the surface of the nailfold and a drop of mineral oil was used as a refractive index matching medium. An objective lens was used to transfer the image from proximal (to the objective) end to the detector. This setup was used to image nailfold capillaries (see A) through a FOP of 0.55 NA. The resulting images (see B) indicate different placement of the FOP on the nailfold indicating different views acquired. The vertical lines indicated the U-shaped capillary loops and some enlargement of the loops was also visible. This may serve as a good indicator for clinical conditions.

The general definition of NA works with the half angle of an imaginary acceptance cone of light that can enter a given system. The NA of an optical fiber is defined by the given equation and links the refractive index of core and cladding to the NA value as described herein. The NA of the aperture is dictated by the radius (or diameter) of the aperture and the height of the aperture as given in the equation, $n_{medium}$ is defined is the refractive index of the surrounding medium.

Throughout the application the following equations are applicable for NA.

General Definition of NA $$NA = n_{medium} \sin \theta_{max}$$

NA of Optical Fiber $$NA_{fiber} = \sqrt{n_{core}^2 - n_{cladding}^2}$$

NA of Aperture $$NA_{aperture} = n_{medium} \times \sin(\theta_{max})$$

where $$\theta_{max} = \tan^{-1} \frac{radius}{height}$$

where $\theta_{max} = \tan^{-1}\frac{radius}{height}$
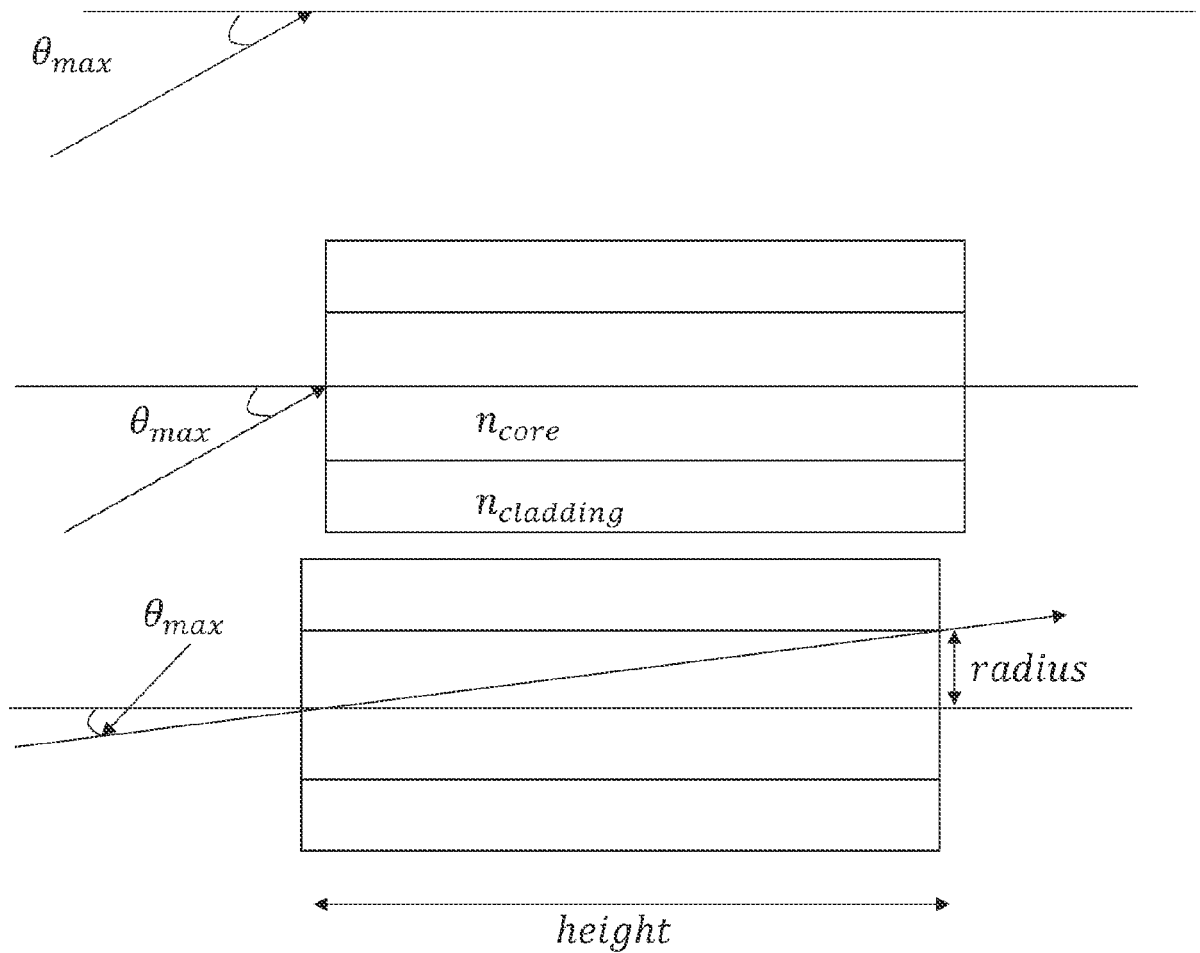

As many changes can be made to the preferred embodiment without departing from the scope thereof, it is intended that all matter contained herein be considered illustrative and not in a limiting sense.

The invention claimed is:

1. A sensing system comprising:
   i) a fibre optic plate (FOP) comprising a proximal end, a distal end and a body situated between said proximal and distal ends and the FOP further comprising at least one optical fibre;
   ii) at least one illumination component; and
   iii) an image sensor proximate to said FOP;
   configured so that said image sensor is about 0.6 to about 50 microns from said proximal end of said FOP and a refractive index matching zone is between said image sensor and said proximal end of said FOP and said at least one optical fibre is arranged longitudinally along the body of said FOP allowing for transmission of an image from one end of said FOP to the other end of said FOP and said at least one optical fibre has a Numerical Aperture (NA) from about 0.0001 to about 0.4, and the FOP has a length of less than about 20 mm and said FOP has light absorbing cladding,
   wherein said image sensor further comprises a dynamic range comprising hardware and software high dynamic range and extended dynamic range, variable hardware pixel binning and a variable frame rate per second (FPS), and said illumination component provides pulse illumination, and said image sensor is a camera with no lens.

2. The system of claim 1, where the at least one optical fibre has a Numerical Aperture (NA) from about 0.0001 to about 0.1.

3. The sensing system of claim 2, wherein said at least one optical fibre is a plurality of optical fibres.

4. The sensing system of claim 3, wherein said image sensor is from about 1 to about 10 microns from said proximal end of said proximal end of said FOP.

5. The sensing system of claim 3, where the at least one illumination component comprises at least one illumination fibre.

6. The sensing system of claim 3, wherein said plurality of optical fibres are bundled together, such that each first end and each second end of said plurality of bundled optical fibres form a grid, and is configured to provide intertwined illumination.

7. The sensing system of claim 3, further comprising a refractive index matching zone between said FOP and said image sensor.

8. The sensing system of claim 3, wherein said refractive index matching zone has a refractive index from about 1.4 to about 1.6.

9. The sensing system of claim 3, wherein said refractive index matching zone is a refractive matching media.

10. The sensing system of claim 3, wherein said image sensor has a pixel size of from 0.6 micron to about 10 microns.

11. The sensing system of claim 3, wherein said image sensor has a pixel size of about 1 micron.

12. The sensing system of claim 3, wherein said image sensor comprises a number of pixels of from 100 to about 10,000,000.

13. The sensing system of claim 3, wherein said plurality of optical fibres has a NA less than or equal to about 0.15.

14. The sensing system of claim 3, further comprising a NA reducer, wherein said FOP has a NA greater than the NA reducer.

15. The sensing system of claim 14, where said NA reducer is at the proximal end of the FOP.

16. The sensing system of claim 14, where said NA reducer is at the distal end of the FOP.

17. The sensing system of claim 3, further comprising the system being configured so the illumination component can be switched between continuous wave illumination or pulse illumination.

18. The sensing system of claim 3, further comprising a human digit receiver.

19. The sensing system of claim 3, further comprising a first NA reducer at the proximal end of the FOP and a second NA reducer at the distal end of the FOP.

* * * * *